United States Patent
Hashimoto

(10) Patent No.: US 10,406,121 B2
(45) Date of Patent: *Sep. 10, 2019

(54) APPLICATION OF R-KETAMINE AND SALT THEREOF AS PHARMACEUTICALS

(71) Applicant: NATIONAL UNIVERSITY CORPORATION CHIBA UNIVERSITY, Chiba (JP)

(72) Inventor: Kenji Hashimoto, Chiba (JP)

(73) Assignee: National University Corporation Chiba University, Chiba (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/849,698

(22) Filed: Dec. 21, 2017

(65) Prior Publication Data
US 2018/0177745 A1 Jun. 28, 2018

Related U.S. Application Data

(63) Continuation of application No. 15/021,003, filed as application No. PCT/JP2014/004730 on Sep. 12, 2014, now Pat. No. 9,872,841.

(30) Foreign Application Priority Data

Sep. 13, 2013 (JP) .................................. 2013-190066

(51) Int. Cl.
A61K 31/135 (2006.01)

(52) U.S. Cl.
CPC .................................. A61K 31/135 (2013.01)

(58) Field of Classification Search
CPC .................................................. A61K 31/135
See application file for complete search history.

(56) References Cited

U.S. PATENT DOCUMENTS

| | | | |
|---|---|---|---|
| 6,040,479 | A | 3/2000 | Steiner et al. |
| 9,872,841 | B2 | 1/2018 | Hashimoto |
| 2012/0225949 | A1 | 9/2012 | Papalos |
| 2016/0220513 | A1 | 8/2016 | Hashimoto |

FOREIGN PATENT DOCUMENTS

| | | |
|---|---|---|
| WO | 2007111880 A2 | 10/2007 |
| WO | 2011020061 A2 | 2/2011 |
| WO | WO 2011/020061 A2 | 2/2011 |

OTHER PUBLICATIONS

Freo et al. Anestheseology, 2004, vol. 100, pp. 1172-1178 (Year: 2004).*

Persson et al. Eur. J. Clin. Pharmacol., 2002, vol. 57, pp. 869-875 (Year: 2002).*

Berman, R. M. et al., "Antidepressant Effects of Ketamine in Depressed Patients," Biological Psychiatry, 47: 351-354 (2000).

Diazgranados, N. et al., "A randomized add-on trial of an N-methyl-D-aspartate antagonist in treatment-resistant bipolar depression," Arch Gen Psychiatry, 67(8): 793-802 (2010).

Diazgranados, N. et al., "Rapid Resolution of Suicidal Ideation After a Single Infusion of an N-Methyl-D-Aspartate Antagonist in Patients With Treatment-Resistant Major Depressive Disorder," J Clin Psychiatry, 71(12): 1605-1611 (2010).

Diniz, B. D. et al., "Late-life depression and risk of vascular dementia and Alzheimer's disease: systematic review and meta-analysis of community-based cohort studies," The British Journal of Psychiatry, 202: 329-335 (2013).

Domino, E. F., "Taming the ketamine tiger," Anesthesiology, 113: 678-684 (2010).

Feder, A. et al., "Efficacy of Intravenous Ketamine for Treatment of Chronic Posttraumatic Stress Disorder: A Randomized Clinical Trial," JAMA Psychiatry, 71(6): 681-388 (2014).

Golden, S. A. et al., "A standardized protocol for repeated social defeat stress in mice," Nature Protocols, 6(8): 1183-1191 (and 1 page corrigendum) (2011).

Hashimoto, K., "Emerging role of glutamate in the pathophysiology of major depressive disorder," Brain Research Reviews, 61: 105-123 (2009).

Krystal, J. H. et al., "Rapid-Acting Glutamatergic Antidepressants: The Path to Ketamine and Beyond," Biol Psychiatry, 73: 1133-1141 (2013).

Lapidus, K. A. et al., "A Randomized Controlled trial of Intranasal Ketamine in Major Depressive Disorder," Biol Psychiatry, 76: 970-976 (2014).

Li, S. X. et al., "Role of the NMDA receptor in cognitive deficits, anxiety and depressive-like behavior in juvenile and adult mice after neonatal dexamethasone exposure," Neurobiology of Disease, 62: 124-134 (2014).

Paslakis, G. et al., "Oral Administration of the NMDA Receptor Antagonist S-Ketamine as Add-On Therapy of Depression: A Case Series," Pharmacopsychiatry, 43: 33-35 (2010).

Paul, R. et al., "Comparison of racemic ketamine and S-ketamine in treatment-resistant major depression: Report of two cases," The World Journal of Biological Psychiatry, 10(3): 241-244 (2009).

Rodriguez, C. I. et al., "Randomized Controlled Crossover Trial of Ketamine in Obsessive-Compulsive Disorder: Proof-of-Concept," Neuropsychopharmacology, 38: 2475-2483 (2013).

Vollenweider, F. X. et al., "Differential psychopathology and patterns of cerebral glucose utilization produced by (S)- and (R)-ketamine in healthy volunteers using positron emission tomography (PET)," Eur. Neuropsychopharmacol. 7: 25-38 (1997).

(Continued)

Primary Examiner — James D. Anderson
(74) Attorney, Agent, or Firm — Cooley LLP; Ivor R. Elrifi; Matthew Pavao

(57) ABSTRACT

Provided is a novel compound having rapid and long-lasting therapeutic effects on diseases exhibiting depressive symptoms. Specifically, provided are an agent for prevention and/or treatment of a depressive symptom, consisting of R(−)-ketamine or a pharmacologically acceptable salt thereof, and a pharmaceutical composition for prevention and/or treatment of a depressive symptom, comprising R(−)-ketamine or a pharmacologically acceptable salt thereof in an effective amount for reducing a depressive symptom, and being substantially free of S(+)-ketamine, and a pharmacologically acceptable salt thereof.

15 Claims, 16 Drawing Sheets

(56) References Cited

OTHER PUBLICATIONS

Wink, L. K. et al., "Intranasal Ketamine Treatment in an Adult With Autism Spectrum Disorder," J Clin Psychiatry, 75(8): 835-836 (2014).

Zarate, C. A. et al., "A Randomized Trial of an N-methyl-d-aspartate Antagonist in Treatment-Resistant Major Depression," Arch Gen Psychiatry, 63: 856-864 (2006).

Schmidt et al., "Cerebral physiological responses to bolus injection of racemic, S(+)-or R(−)-ketamine in the pig," Acta Anaesthesiologica Scandinavica, vol. 49, No. 10, Oct. 13, 2005, pp. 1436-1442.

Irwin et al., "Daily Oral Ketamine for the Treatment of Depression and Anxiety in Patients Receiving Hospice Care: A 28-Day Open-Label Proof-of-Concept Trial," Journal of Palliative Medicine, vol. 16, No. 8, Aug. 2013, pp. 958-965.

Paul et al., "Comparison of racemic ketamine and S-ketamine in treatment-resistant major depression: Report of two cases," The World Journal of Biological Psychiatry, vol. 10, No. 3, Jan. 1, 2009, pp. 241-244.

Womble, A.L., "Effects of Ketamine on Major Depressive Disorder in a Patient With Posttraumatic Stress Disorder,"AANA Journal, vol. 81, No. 2, Apr. 2013, pp. 118-119.

Zhang et al., "R (−)-ketamine shows greater potency and longer lasting antidepressant effects than S (+)-ketamine," Pharmacology Biochemistry and Behavior, vol. 116, Jan. 1, 2014, pp. 137-141.

International Search Report issued in corresponding International Patent Application No. PCT/JP2014/004730 dated Jan. 12, 2015 (5 pages).

International Preliminary Report on Patentability and Written Opinion issued in corresponding International Patent Application No. PCT/JP2014/004730 dated Mar. 15, 2016 (8 pages).

Bloch et al., Bio. Psychiatry, 2012, vol. 72, pp. 964-970.

White et al., Br. J. Anaesth., 1985, vol. 57, pp. 197-203.

Graf et al., Anesthesiology, 1995, 82(6), pp. 1426-1437.

\* cited by examiner

[Fig. 1]
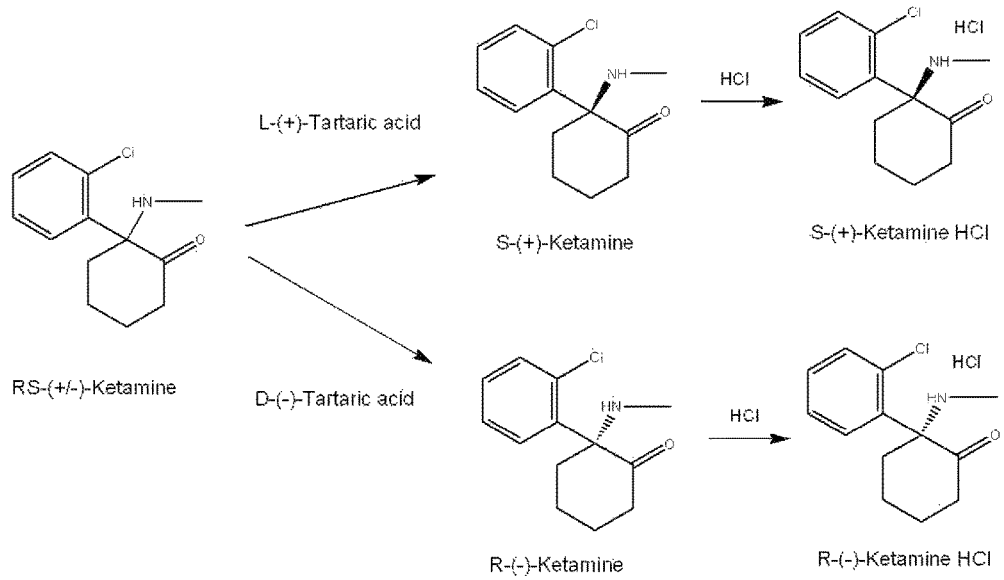
[Fig. 2A]
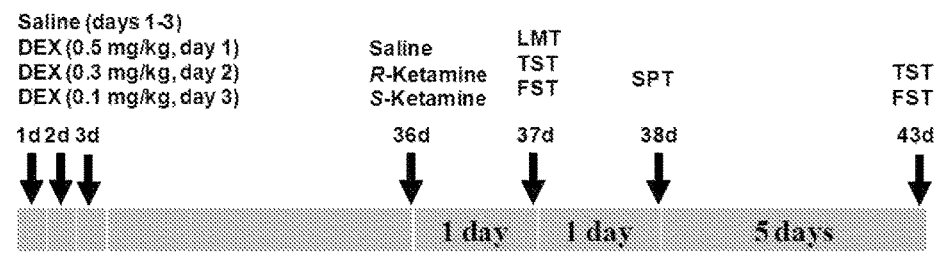
DEX: dexamethasone. LMT: locomotion test. TST: tail suspension test.
FST: force swimming test. SPT: 1% sucrose preference test.
[Fig. 2B]
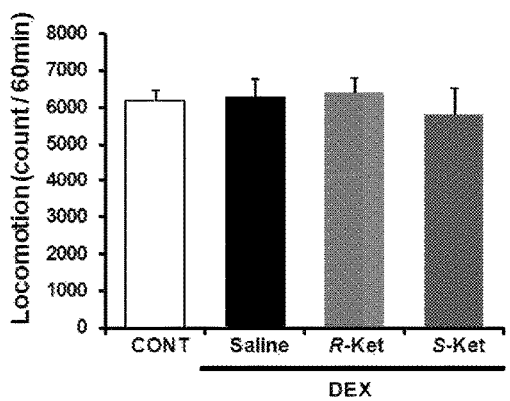

[Fig. 2C]
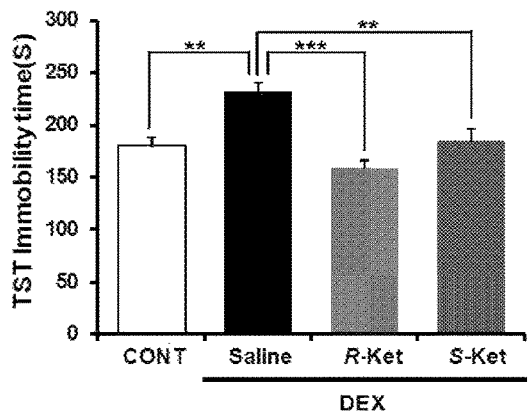
[Fig. 2D]
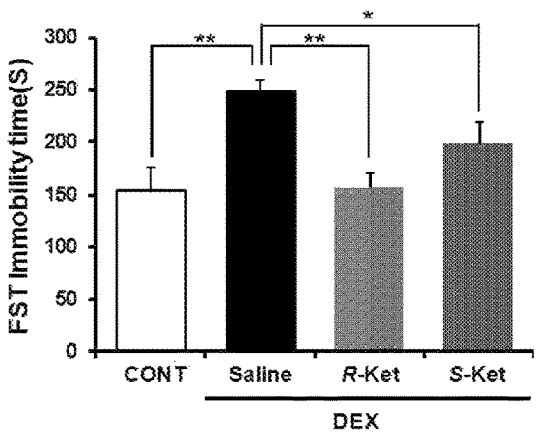
[Fig. 2E]
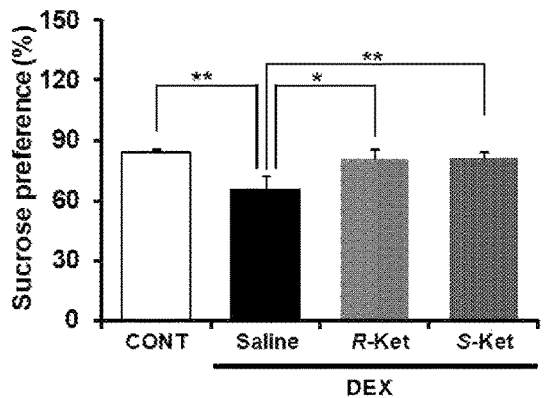

[Fig. 2F]
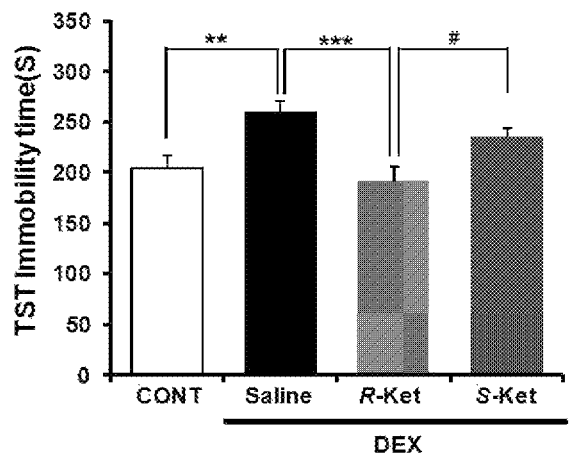
[Fig. 2G]
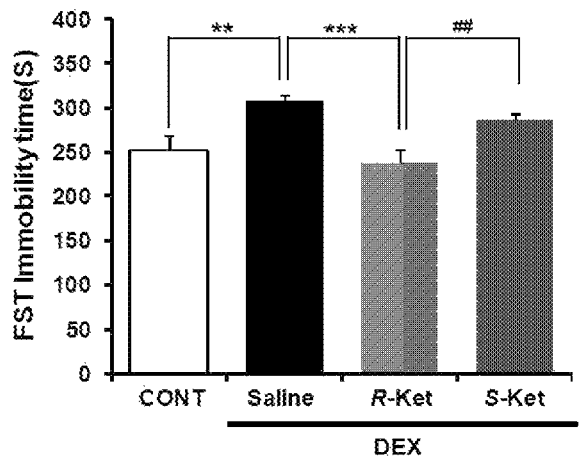
[Fig. 3A]
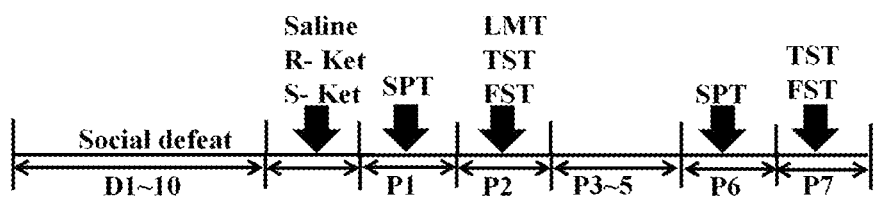
R-Ket: R-ketamine. S-Ket: S-ketamine. SPT: 1% sucrose preference test.
LMT: locomotion test. TST: tail suspension test. FST: force swimming test.

[Fig. 3B]
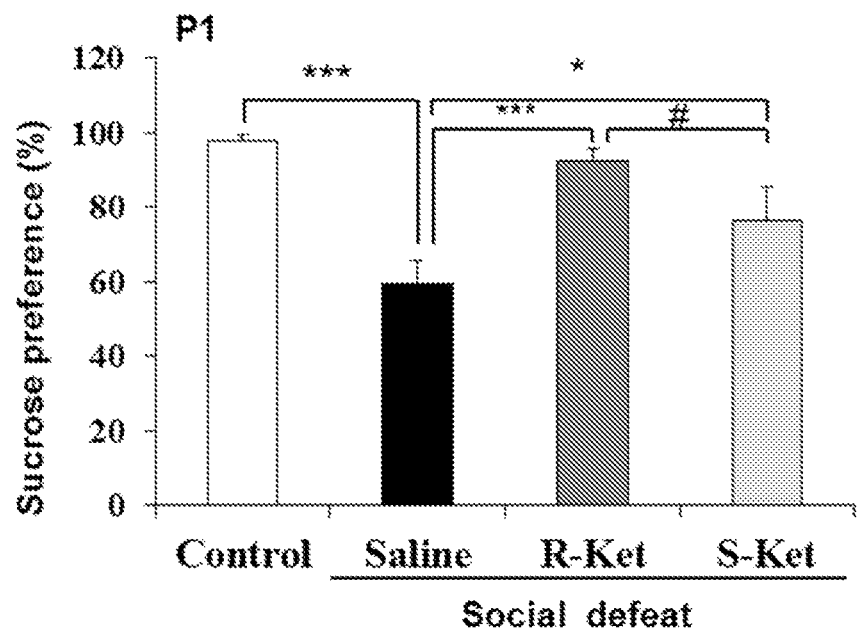
[Fig. 3C]
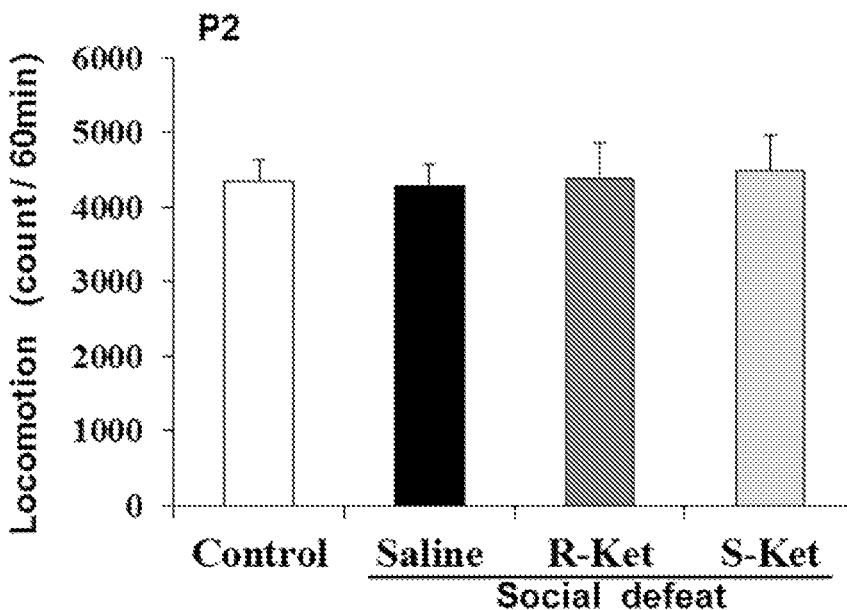

[Fig. 3D]
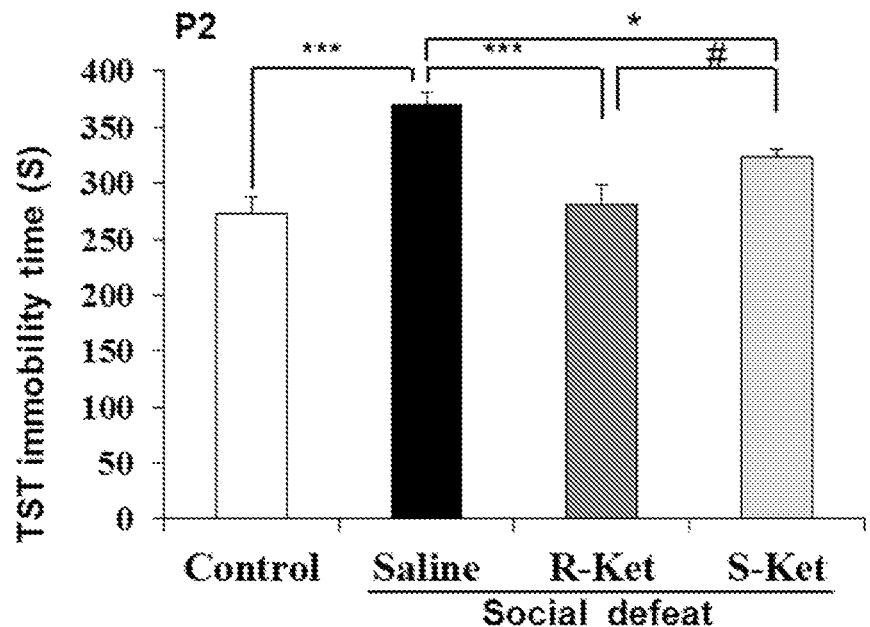
[Fig. 3E]
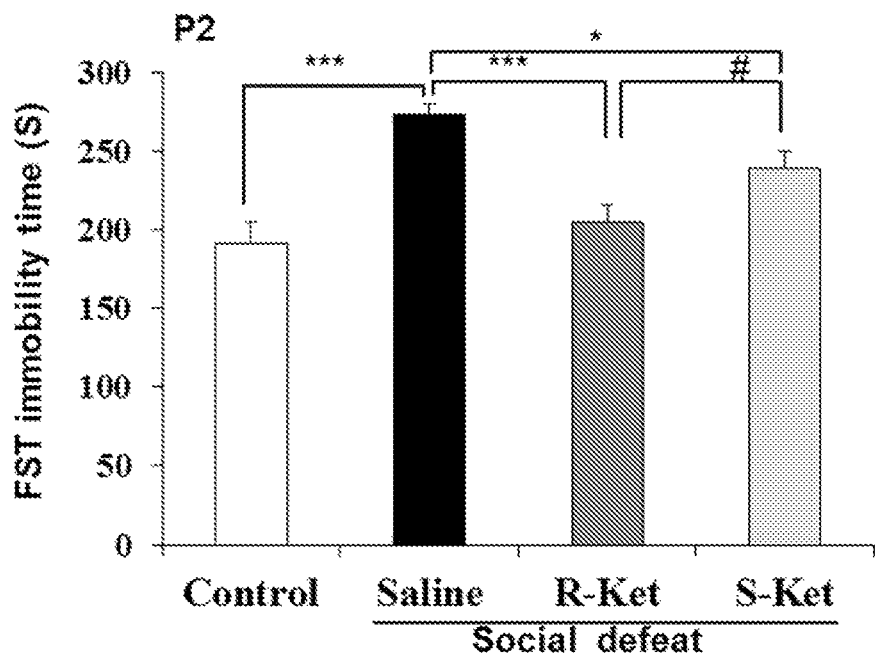

[Fig. 3F]
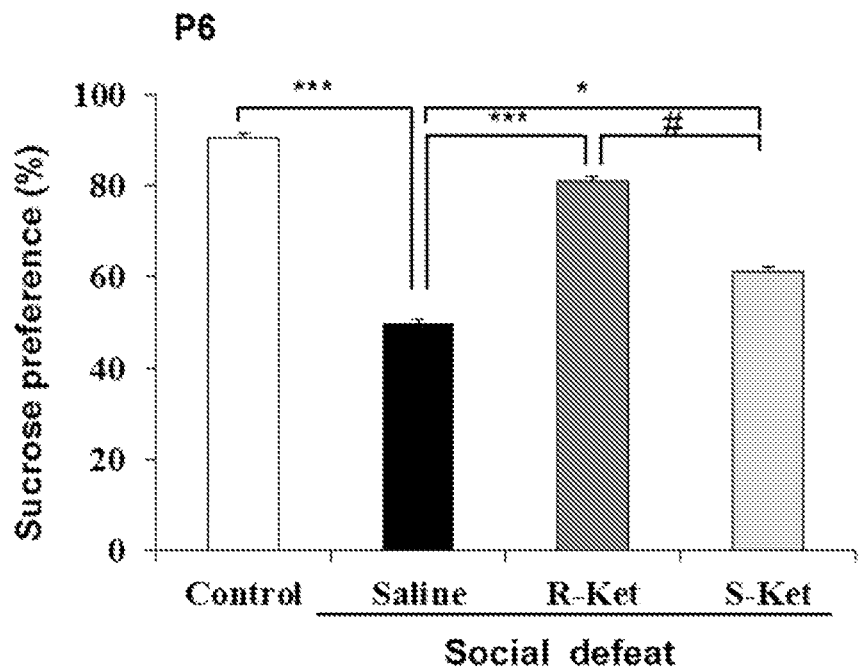
[Fig. 3G]
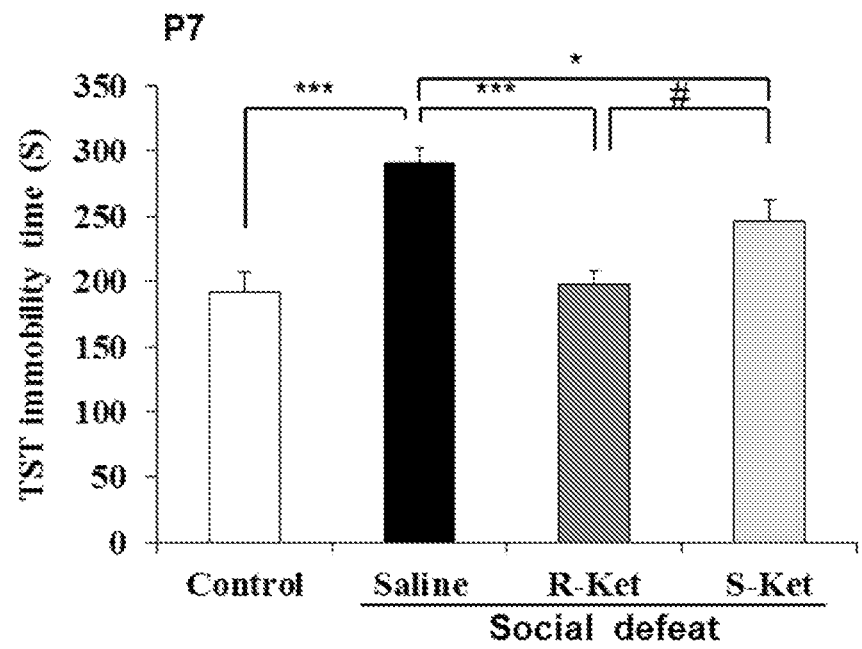

[Fig. 3H]
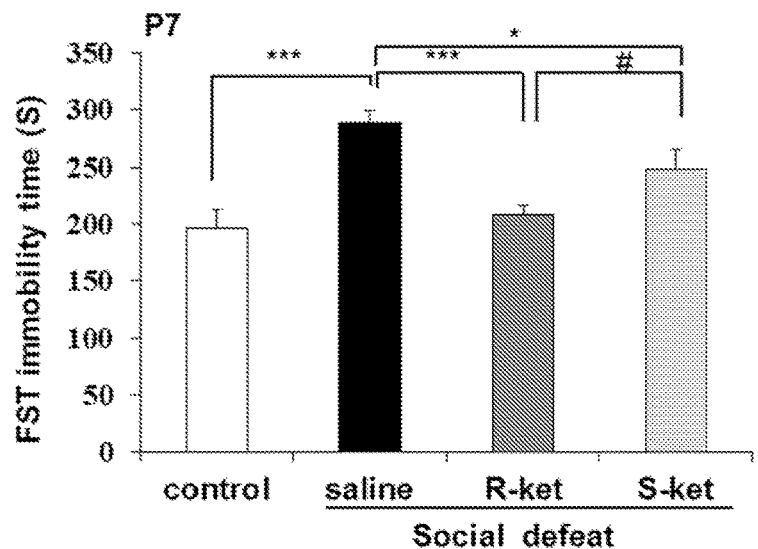
[Fig. 3I]
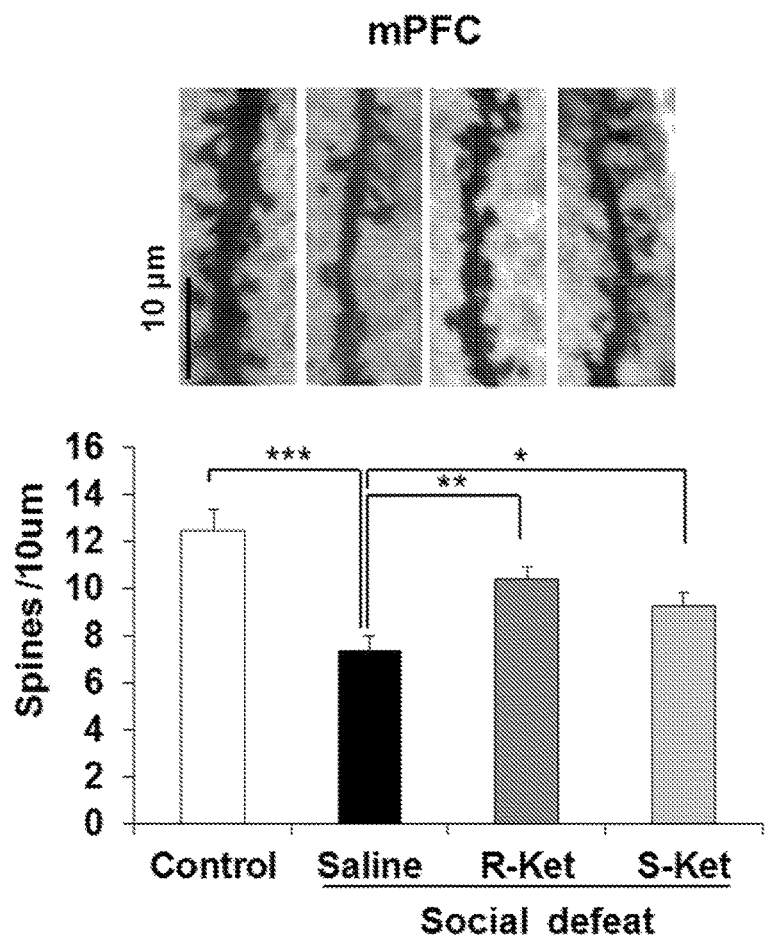

[Fig. 3J]
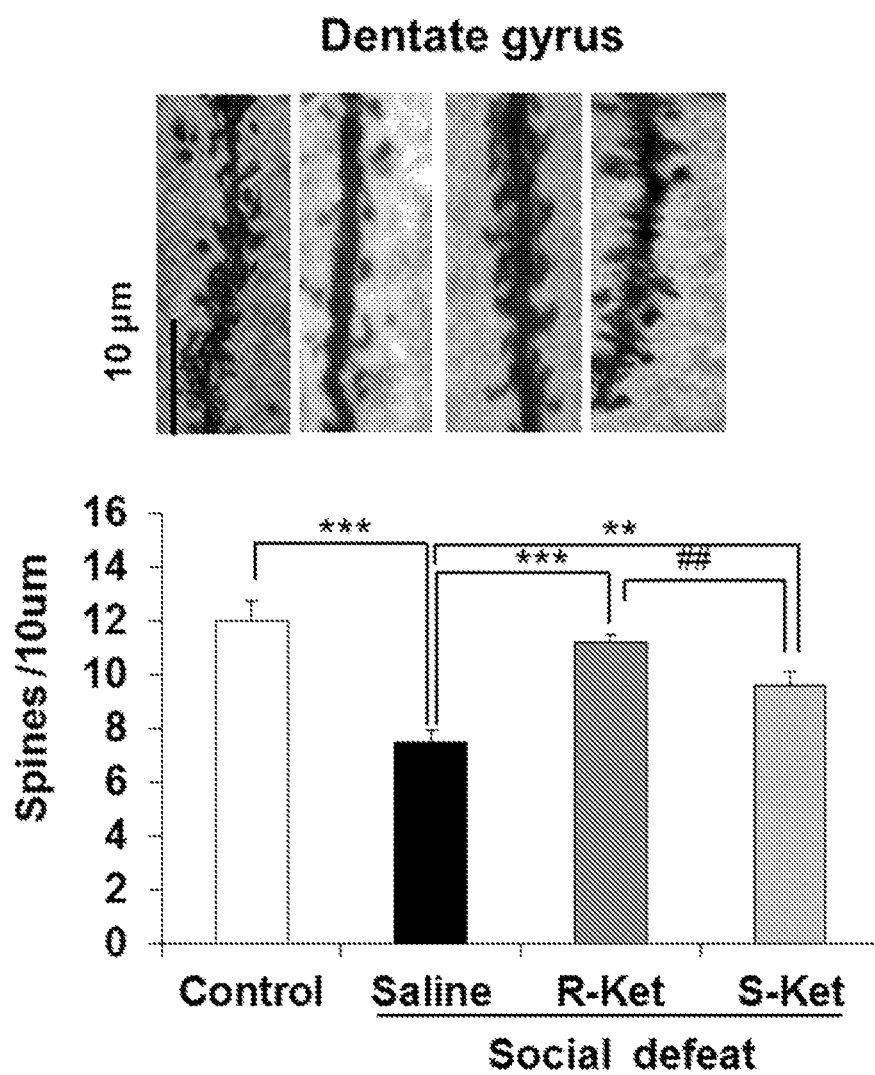

[Fig. 3K]
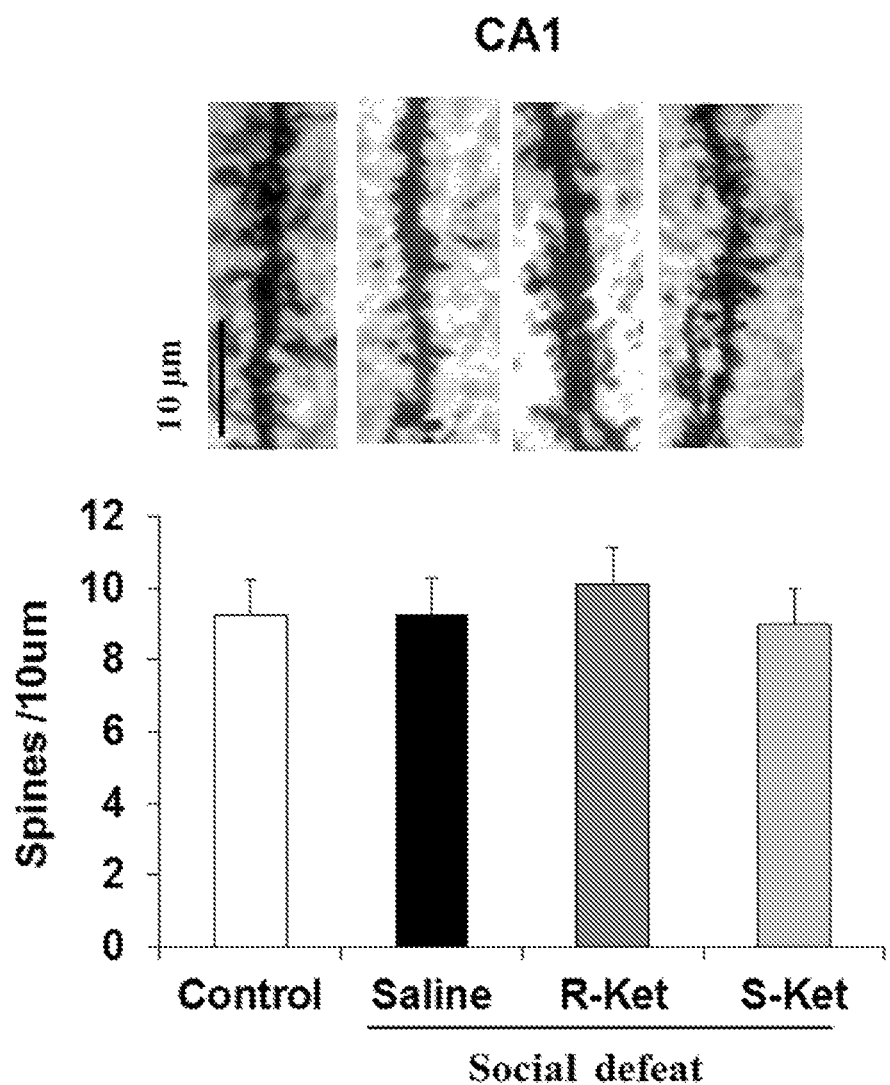

[Fig. 3L]
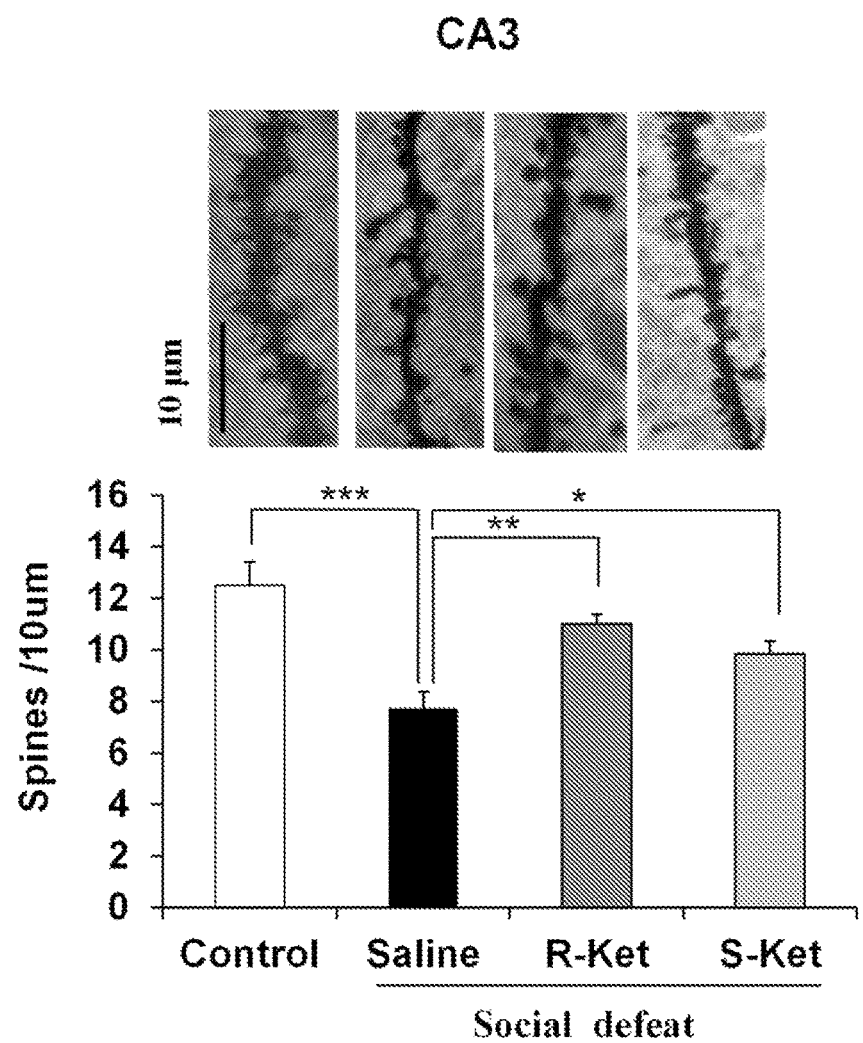

[Fig. 3M]
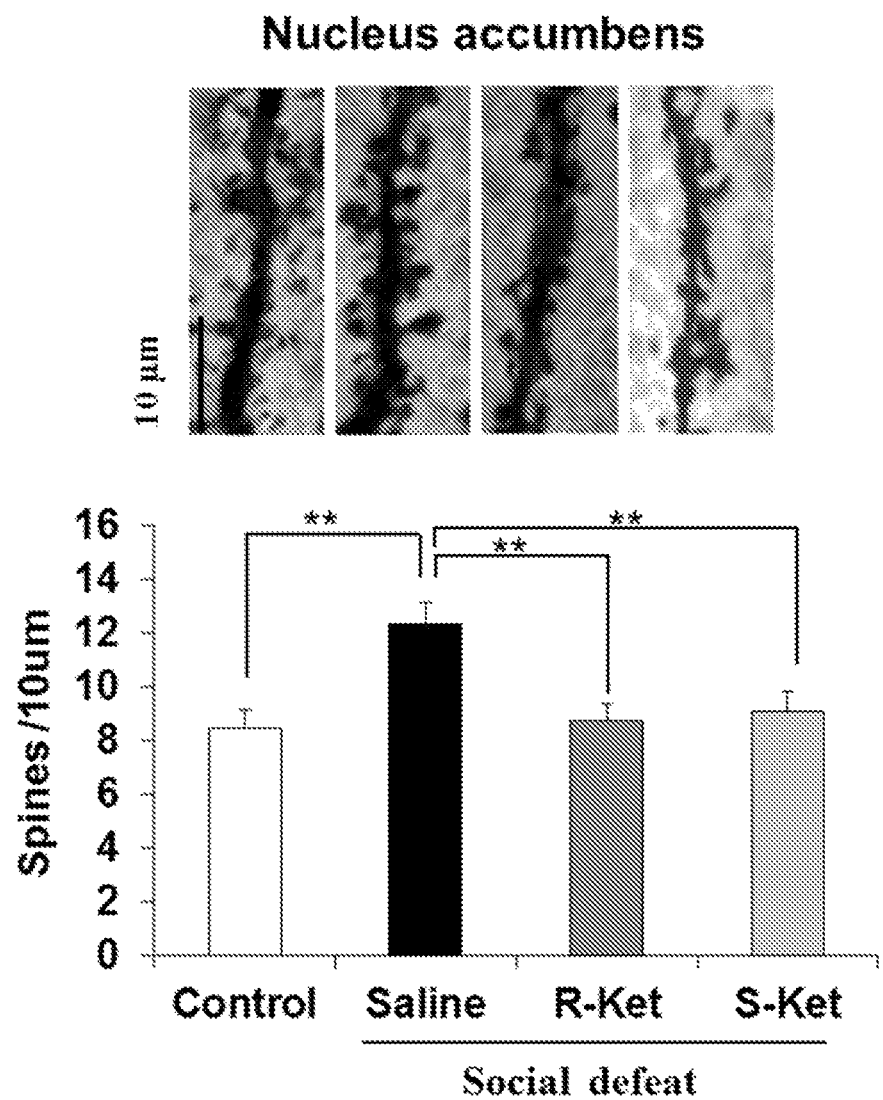

[Fig. 3N]
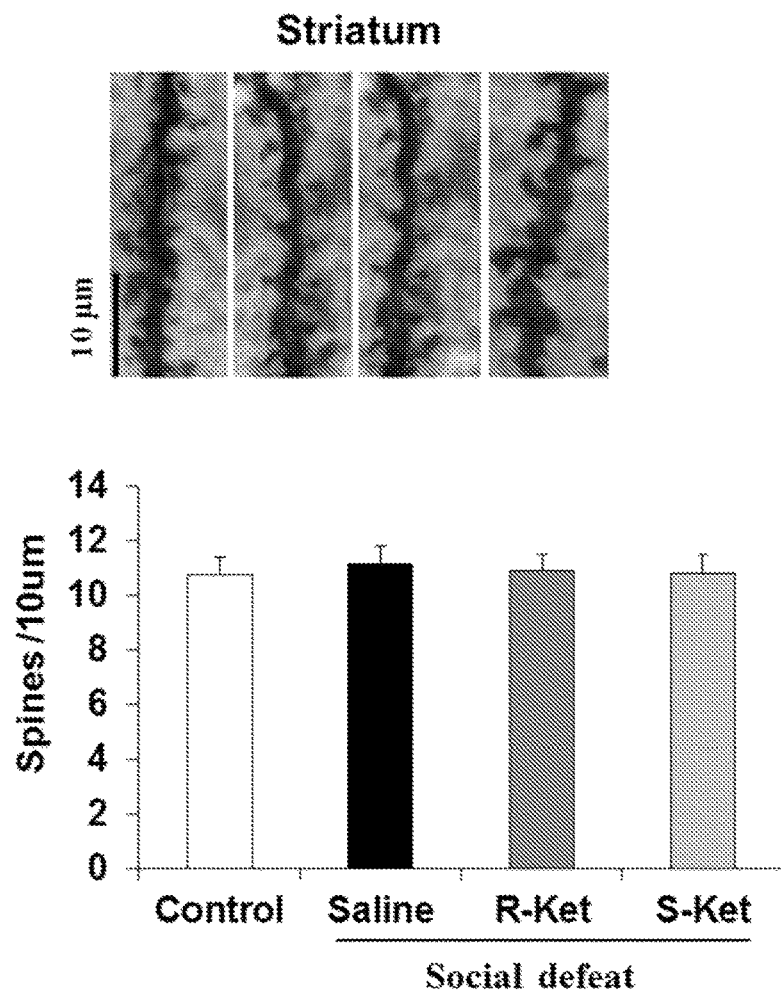
[Fig. 4]
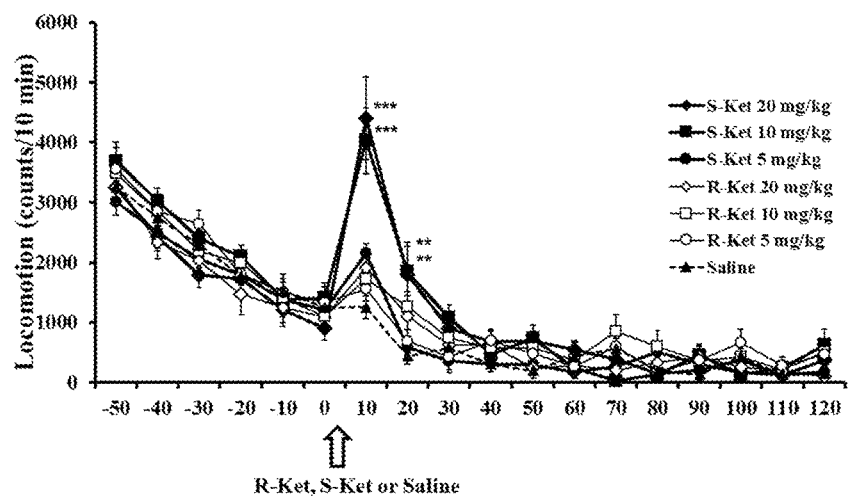

[Fig. 5A]
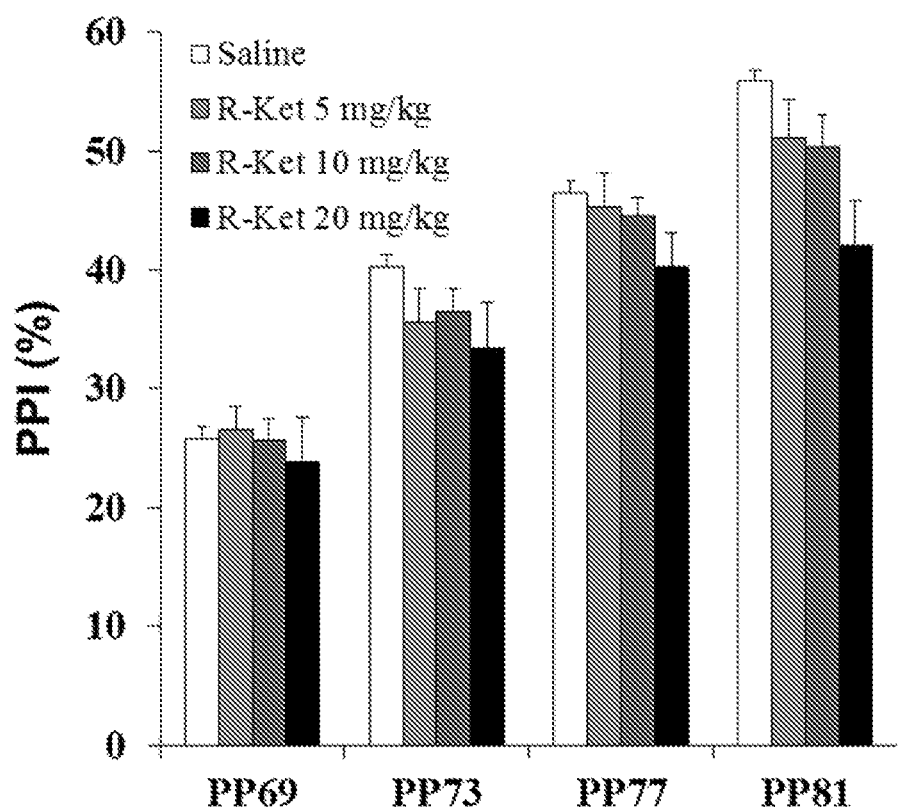

[Fig. 5B]
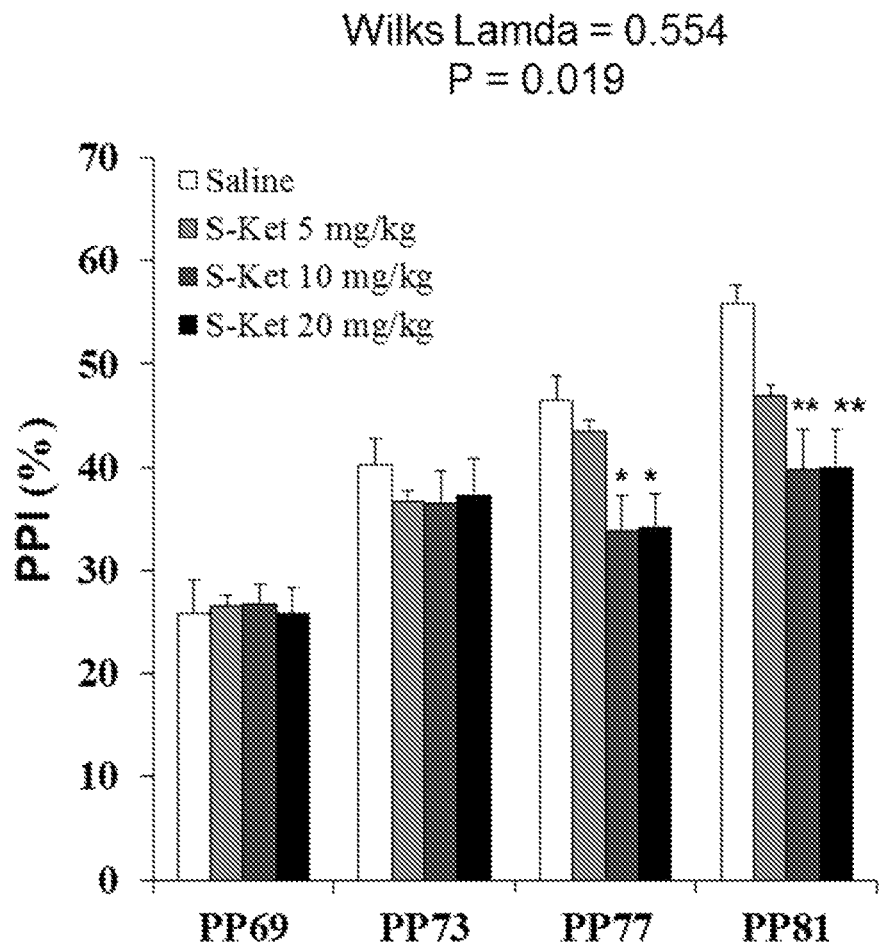
[Fig. 6A]
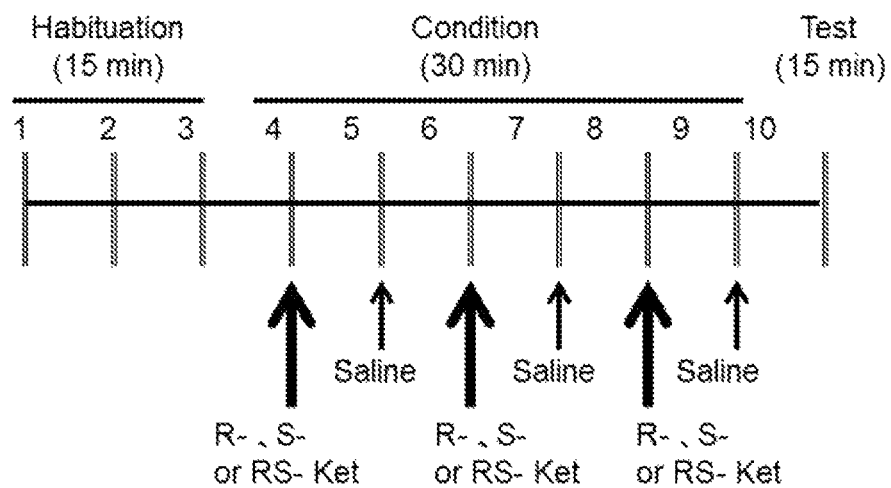

[Fig. 6B]
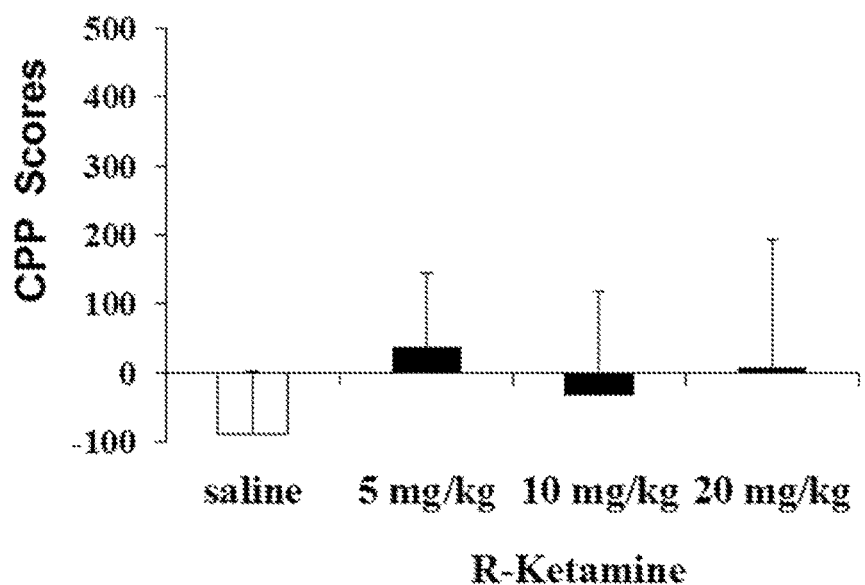
[Fig. 6C]
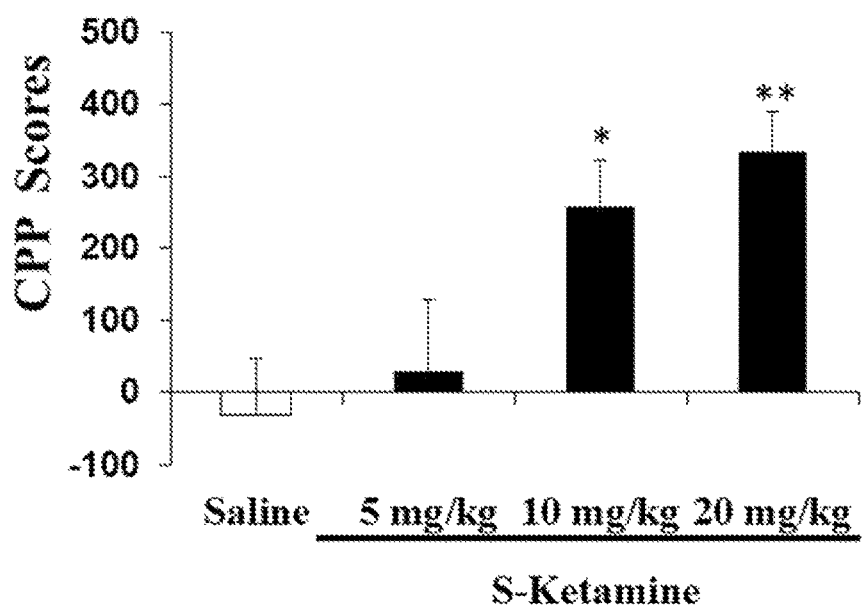

[Fig. 6D]
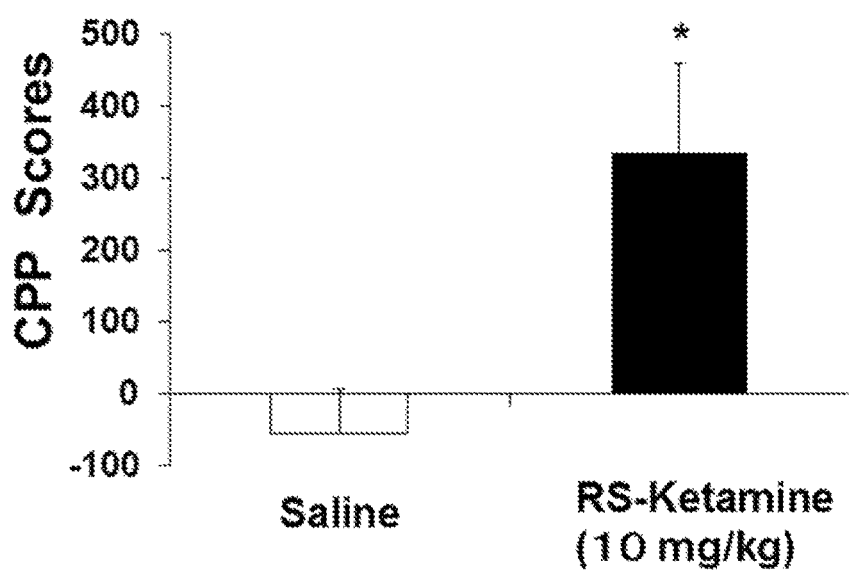

APPLICATION OF R-KETAMINE AND SALT THEREOF AS PHARMACEUTICALS

The present application is a continuation of U.S. patent application Ser. No. 15/021,003 filed Mar. 10, 2016, which is a National Stage Application of PCT/JP2014/004730, filed Sep. 12, 2014, which claims foreign priority based on Japanese Patent Application No. 2013-190066, filed Sep. 13, 2013.

TECHNICAL FIELD

The present invention relates to a pharmaceutical for prevention and/or treatment of psychiatric diseases, preferably diseases exhibiting depressive symptoms. More specifically, the present invention relates to an antidepressant including R-ketamine or a pharmaceutically acceptable salt thereof, and to a pharmaceutical composition for prevention and/or treatment of diseases exhibiting depressive symptoms, including R-ketamine or a pharmaceutically acceptable salt thereof, and being substantially free of S-ketamine or a pharmaceutically acceptable salt thereof.

BACKGROUND ART

Along with changes in social life style and aging of society, various diseases such as psychiatric diseases and neurological diseases tend to increase as a whole. For example, high incidences of depression and schizophrenia, which are major psychiatric diseases, have become a serious problem from the viewpoint of medical economy as well. In addition, obsessive-compulsive disorder is an anxiety disorder involving obsessions and compulsions. In treatment of the psychiatric diseases such as depression, schizophrenia, anxiety disorders, and autism spectrum disorder, medication is essential, and an antidepressant (e.g., a tricyclic antidepressant, a selective serotonin reuptake inhibitor, and a serotonin and norepinephrine reuptake inhibitor), an antipsychotic (e.g., a phenothiazine-based compound, a butyrophenone-based compound, a benzamide-based compound, an iminodibenzyl compound, a thiepin-based compound, an indole-based compound, and a serotonin/dopamine receptor antagonist), and an anti-anxiety drug are administered. However, those drugs used actually in a clinical field are effective for some patients and some symptoms, but patients for whom the drugs are ineffective, so-called treatment-resistant patients are also known to exist. Thus, there is a strong demand for development of a novel therapeutic drug. It is hard to say that the existing drugs exhibit sufficient therapeutic effects on those psychiatric diseases. In reality, there are substantially no effective prevention and treatment methods at present.

One of the major problems in treatment of depression is that there are limitations on effects of the antidepressant and effects of its adjuvant therapy. It takes several weeks or more for the current antidepressants to express their drug efficacy. In addition, there exist treatment-resistant patients for whom those antidepressants are ineffective. Therefore, it is also said that only 50% of patients with depression reach remission. In addition, when a dose of the antidepressant is increased for achieving remission, a patient suffers from various side effects accordingly. Further, depression is one of the cause of suicide. Depression in elderly peoples is known to increase the risk if incident dementia, in particular of Alzheimer's disease and vascular dementia (Non Patent Literature 1).

In recent research, growing evidence suggests that abnormality in glutamatergic transmission, in particular, glutamatergic neurotransmission via an N-methyl-D-aspartate (hereinafter abbreviated as NMDA) receptor is associated with pathophysiology of mood disorders such as major depressive disorder (hereinafter abbreviated as MDD) and bipolar disorder. The MNDA receptor also plays key roles in neurobiology and treatment of MDD as well (Non Patent Literature 2).

It has been reported that an NMDA receptor antagonist ketamine exhibits rapid and robust antidepressant effects on treatment-resistant patients with MDD and depressive symptoms of treatment-resistant bipolar disorder (Non Patent Literatures 3 to 5). In addition, it has been reported that ketamine is also effective for treatment-resistant obsessive-compulsive disorder and treatment-resistant posttraumatic stress disorder (hereinafter abbreviated as PTSD) (Non Patent Literatures 6 to 8). Ketamine has also been reported to have an effect of inhibiting suicide ideation (Non Patent Literature 9). Further, ketamine treatment in an adult with autism spectrum has been reported (Non Patent Literature 10). Ketamine, which was a compound developed as an anesthetic in 1962, started to be applied clinically in 1965. However, ketamine is designated as a controlled substance because of its problems of psychotic symptoms such as hallucination and delusion, and drug dependence. At present, ketamine is used as an anesthetic and for treatment of chronic pain in a clinical field.

It has been reported that clinical antidepressant effects of ketamine last for a short period of from 1 to 2 days starting from several hours after its single administration. Meanwhile, it has been reported that the effects may last over 2 weeks or more (Non Patent Literatures 3, 4, and 11). In addition, it has been reported that ketamine has psychotomimetic effects as side effects, and antidepressant effects of ketamine were not present until after the side effects had disappeared (Non Patent Literatures 3 and 4).

Ketamine (or sometimes referred to as RS(+/−)-ketamine) is a racemic mixture containing equal amounts of R(−)-ketamine and S(+)-ketamine. R(−)-ketamine and S(+)-ketamine are also called R-isomer and S-isomer of ketamine, respectively. S(+)-ketamine has approximately 4-fold greater affinity for the NMDA receptor than R-isomer (Non Patent Literature 12). Further, S(+)-ketamine has an approximately 3- to 4-fold anesthetic effect as compared to R-isomer, and has greater psychotomimetic side effects than R-isomer (Non Patent Literature 12). As described above, the potency of psychotomimetic effects of ketamine is correlated with the potency of blockade of the NMDA receptor (Non Patent Literature 12). A positron emission tomography (PET) study in healthy volunteers demonstrated that psychotomimetic doses of S(+)-ketamine (i.e., intravenous infusion of 15 mg for 5 min, then infusion of the dose (0.014 to 0.02 mg/kg/min for 53 min) increased cerebral metabolic rates of glucose (hereinafter abbreviated as CMR-glu) markedly in the frontal cortex and thalamus (Non Patent Literature 13). In contrast, equimolar doses of R(−)-ketamine tended to decrease CMRglu across brain regions, and did not produce psychotic symptoms, but a state of relaxation and a feeling of well being (Non Patent Literature 13).

As described above, it is generally understood that both analgesic effects and psychotomimetic effects of ketamine are mediated primarily via the blockade of the NMDA receptor. S-isomer of ketamine has high affinity for the NMDA receptor. Thus, it is considered that those effects of ketamine are caused primarily by S-isomer.

At present, ketamine is one of the drugs that have attracted attention for treatment of treatment-resistant patients with MDD, depressive symptoms of treatment-resistant bipolar disorder, treatment-resistant obsessive-compulsive disorder, and treatment-resistant PTSD (Non Patent Literatures 5 to 12). A previous case report showed that antidepressant effects of S(+)-ketamine (0.25 mg/kg, i.v.) in treatment-resistant patients with MDD were weaker than those of RS(+/−)-ketamine (0.5 mg/kg, i.v.) (Non Patent Literature 14). Further, an open label study (Non Patent Literature 15) and a case report (Non Patent Literature 16) showed that effective oral doses of RS(+/−)-ketamine and S(+)-ketamine in patients with depression were 0.5 mg/kg and 1.25 mg/kg, respectively. In addition, intranasal administration of ketamine showed antidepressant effect in treatment-resistant patients with MDD (Patent Literature 1 and Non Patent Literature 17).

CITATION LIST

Patent Literature

[PTL 1] International Patent Publication No. WO 2007/111880 A2
[PTL 2] U.S. Pat. No. 6,040,479 (A)

Non Patent Literature

[NPL 1] Diniz B D, Butters M A, Albert S M, Dew M A and Reynolds C F (2013) Late-life depression and risk of vascular dementia and Alzheimer's disease: systematic review and meta-analysis of community-based cohort studies. B. J. Psychiatry 202: 329-335.
[NPL 2] Hashimoto K (2009) Emerging role of glutamate in the pathophysiology of major depressive disorder. Brain Res. Rev. 61:105-23.
[NPL 3] Berman R M, Cappiello A, Anand A, Oren D A, Heninger G R, Charney D S, Krystal J H (2000) Antidepressant effects of ketamine in depressed patients. Biol. Psychiatry 47:351-4.
[NPL 4] Zarate C A, Jr, Singh J B, Carlson P J, Brutsche N E, Ameli R, Luckenbaugh D A, Charney D S, Manji H K (2006) A randomized trial of an N-methyl-D-aspartate antagonist in treatment-resistant major depression. Arch. Gen. Psychiatry 63:856-64.
[NPL 5] Diazgranados N, Ibrahim L, Brutsche N E, Newberg A, Kronstein P, Khalife S, Kammerer W A, Quezado Z, Luckenbaugh D A, Salvadore G, Machado-Vieira R, Manji H K, Zarate C A Jr. (2010) A randomized add-on trial of an N-methyl-D-aspartate antagonist in treatment-resistant bipolar depression. Arch. Gen. Psychiatry 67:793-802.
[NPL 6] Bloch M H, Wasylink S, Landeros-Weisenberger A, Panza K E, Billingslea E, Leckman J F, Krystal J H, Bhagwagar Z, Sanacora G, Pittenger C (2012) Effects of ketamine in treatment-refractory obsessive-compulsive disorder. Biol. Psychiatry 72(11):964-970.
[NPL 7] Rodriguez C I, Kegeles L S, LevinsonA, Feng T, Marcus S M, Vermes D, Flood P, Simpson H B (2013) Randomized Controlled Crossover Trial of Ketamine in Obsessive-Compulsive Disorder: Proof-of-Concept. Neuropsychopharmacology 38:2475-83.
[NPL 8] Feder A, Parides M K, Murrough J W, Perez A M, Morgan J E, Saxena S, Kirkwood K, Aan Het Rot M, Lapidus K A, Wan L B, Iosifescu D, Charney D S (2014) Efficacy of intravenous ketamine for treatment of chronic posttraumatic stress disorder: a randomized clinical trial. JAMA Psychiatry 71:681-688.
[NPL 9] DiazGranados N, Ibrahim L A, Brutsche N E, Ameli R, Henter I D, Luckenbaugh D A, Machado-Vieira R, Zarate C A Jr (2010) Rapid resolution of suicidal ideation after a single infusion of an N-methyl-D-aspartate antagonist in patients with treatment-resistant major depressive disorder. J Clin. Psychiatry 71(12):1605-11.
[NPL 10] Wink L K I, O'Melia A M, Shaffer R C, Pedapati E, Friedmann K, Schaefer T, Erickson C A (2014) Intranasal ketamine treatment in an adult with autism spectrum disorder. J Clin. Psychiatry 75(8):835-6. doi: 10.4088/JCP.13cr08917.
[NPL 11] Krystal J H, Sanacora G, Duman R S (2013) Rapid-acting glutamatergic antidepressants: the path to ketamine and beyond. Biol. Psychiatry 73:1133-41.
[NPL 12] Domino E F (2010) Taming the ketamine tiger. 1965. Anesthesiology 113:678-86.
[NPL 13] Vollenweider F X, Leenders K L, OEye I, Hell D, Angst J (1997) Differential psychopathology and patterns of cerebral glucose utilization produced by (S)- and (R)-ketamine in healthy volunteers using positron emission tomography (PET). Eur. Neuropsychopharmacol. 7: 25-38.
[NPL 14] Paul R, Schaaff N, Padberg F, Moeller H J, Frodl T (2009) Comparison of racemic ketamine and S-ketamine in treatment-resistant major depression: report from two cases. World J. Biol. Psychiatry 10: 241-244.
[NPL 15] Paslakis G, Gilles M, Meyer-Lindenberg A, Deuschle M (2010) Oral administration of the NMDA receptor antagonist S-ketamine as add-on therapy of depression: a case series. Pharmacopsychiatry 43: 33-35.
[NPL 16] Irwin S A, Iglewicz A, Nelesen R A, Lo J Y, Carr C H, Romero S D, Lloyd L S (2013) Daily oral ketamine for the treatment of depression and anxiety in patients receiving hospice care: A 28-day open-label proof-of-concept trial. J. Palliat. Med. 16: 958-965.
[NPL 17] Lapidus K A, Levitch C F, Perez A M, Brallier J W, Parides M K, Soleimani L, Feder A, Iosifescu D V, Charney D S, Murrough J W (2014) A randomized controlled trial of intranasal ketamine in major depressive disorder. Biol. Psychiatry 2014 Apr. 3. pii: 50006-3223 (14)00227-3.doi: 10.1016/j.biopsych.2014.03.026. [Epub ahead of print]
[NPL 18] Li S X, Fujita Y, Zhang J C, Ren Q, Ishima T, Wu J, Hashimoto K (2014) Role of the NMDA receptor in cognitive deficits, anxiety and depressive-like behavior in juvenile and adult mice after neonatal dexamethasone exposure. Neurobiol. Dis. 62: 124-134.
[NPL 19] Golden S A, Covington H E, III, Berton O, Russo S J (2011) A standardized protocol for repeated social defeat stress in mice. Nat. Protoc. 6: 1183-1191.

SUMMARY OF INVENTION

Technical Problem

It has been reported that the NMDA receptor antagonist ketamine exhibits rapid antidepressant effects in treatment-resistant patients with depression. The glutamatergic neurotransmission via the NMDA receptor is considered to be involved in depression, ketamine includes optical isomers, i.e., S-isomer and R-isomer, and S-isomer has higher affinity for the NMDA receptor than R-isomer. Thus, S-isomer or a racemic mixture has been used for research on treatment of depression with ketamine. However, ketamine has problems of side effects including psychotic symptoms such as hallucination and delusion, and dependence, and is designated as a controlled substance. Accordingly, it is difficult to practically use ketamine in a clinical field.

An object of the present invention is to provide a novel compound having rapid and long-lasting antidepressant effects on diseases exhibiting depressive symptoms, such as depression, bipolar disorder, obsessive-compulsive disorder, PTSD, and autism spectrum disorder.

Solution to Problem

The inventors of the present invention have made intensive studies in order to achieve the above-mentioned object. In the studies, the inventors have focused attention on R(−)-ketamine, which has not been used for research on antidepressant effects of ketamine heretofore. In addition, in research using a mouse model of depression, the inventors have found that R(−)-ketamine exhibits more potent antidepressant effects on the depression-like symptoms of the mouse model at a juvenile stage than S(+)-ketamine, and the effects last for a longer period. The inventors also found in social defeat stress model mice that R(−)-ketamine showed more potent and long lasting anti-depressant effect compared to S(+)-ketamine. Furthermore, administration of S(+)-ketamine induced some side effects such as a hyper-locomotion, prepulse inhibition deficit, and drug dependence, while administration of R(−)-ketamine did not. Since R-isomer of ketamine has low affinity for an NMDA receptor as compared to its S-isomer, the R-isomer is considered to have less psychotomimetic effects as side effects and to hardly produce drug dependence. The present invention has been accomplished based on those findings.

That is, the present invention relates to an agent for prevention and/or treatment of a depressive symptom, consisting of R(−)-ketamine or a pharmacologically acceptable salt thereof.

The present invention also relates to the agent, in which the depressive symptom is a depressive symptom in depression in children or adults.

The present invention also relates to a pharmaceutical composition for prevention and/or treatment of a depressive symptom, comprising R(−)-ketamine or a pharmacologically acceptable salt thereof in an effective amount for reducing a depressive symptom, and being substantially free of S(+)-ketamine or a pharmacologically acceptable salt thereof.

The present invention also relates to the pharmaceutical composition, in which the depressive symptom is a depressive symptom in depression in children or adults.

The present invention also relates to a pharmaceutical composition for prevention and/or treatment of obsessive-compulsive disorder, comprising R(−)-ketamine or a pharmacologically acceptable salt thereof in an effective amount for reducing a depressive symptom in obsessive-compulsive disorder, and being substantially free of S(+)-ketamine or a pharmacologically acceptable salt thereof.

The present invention also relates to a pharmaceutical composition for prevention and/or treatment of posttraumatic stress disorder, comprising R(−)-ketamine or a pharmacologically acceptable salt thereof in an effective amount for reducing a depressive symptom in posttraumatic stress disorder, and being substantially free of S(+)-ketamine or a pharmacologically acceptable salt thereof.

The present invention also relates to a method of treating a depressive symptom, comprising administering R(−)-ketamine or a pharmacologically acceptable salt thereof to a subject, wherein the subject has been diagnosed with having a depressive symptom, in an amount effective to treat the depressive symptom.

The present invention also relates to the method, in which the subject has been diagnosed with depression in children or adults The present invention also relates to the method, in which the subject has been diagnosed with obsessive-compulsive disorder.

The present invention also relates to the method, in which the subject has been diagnosed with posttraumatic stress disorder.

The present invention also relates to a method of treating a depressive symptom, comprising administering a pharmaceutical composition to a subject, wherein the pharmaceutical composition comprises R(−)-ketamine or a pharmaceutically acceptable salt thereof in an amount effective to treat a depressive symptom, and a pharmaceutically acceptable carrier, and being substantially free of S(+)-ketamine or a pharmacologically acceptable salt thereof, and wherein the subject has been diagnosed with having a depressive symptom.

The present invention also relates to the method, in which the subject has been diagnosed with depression in children or adults.

The present invention also relates to the method, in which the subject has been diagnosed with obsessive-compulsive disorder.

The present invention also relates to the method, in which the subject has been diagnosed with posttraumatic stress disorder.

The present invention also relates to use of R(−)-ketamine for the manufacture of a pharmaceutical composition for treating a depressive symptom.

The present invention also relates to the use, in which the depressive symptom accompanies depression in children or adults.

The present invention also relates to the use, in which the depressive symptom accompanies obsessive-compulsive disorder.

The present invention also relates to the use, in which the depressive symptoms accompanies posttraumatic stress disorder.

Advantageous Effects of Invention

R(−)-ketamine or a pharmaceutically acceptable salt thereof has rapid and long-lasting antidepressant effects and less side effects, and hence is effective for prevention and/or treatment of psychiatric diseases exhibiting depressive symptoms. Accordingly, the agent consisting of R(−)-ketamine or a pharmacologically acceptable salt thereof, and the pharmaceutical composition including R(−)-ketamine or a pharmacologically acceptable salt thereof, and being substantially free of S(+)-ketamine or a pharmacologically acceptable salt thereof are useful as novel pharmaceuticals in the field of prevention and/or treatment of psychiatric diseases exhibiting depressive symptoms.

BRIEF DESCRIPTION OF DRAWINGS

FIG. 1 is a diagram illustrating the preparation of R(−)- and S(+)-ketamine hydrochloride (Ketamine HCl) from RS(+/−)-ketamine using D(−)- and L(+)-tartaric acid (Tartaric acid), respectively.

FIG. 2A is a diagram illustrating a test protocol for investigating antidepressant effects of R(−)- and S(+)-ketamine. Tests were performed using mice treated neonatally with dexamethasone (hereinafter referred to as DEX-treated mice) as a new animal model of depression. In FIG. 2A, DEX means dexamethasone, LMT means a locomotion test, TST means a tail suspension test, FST means a forced swimming test, and SPT means a 1% sucrose preference test. (Example 1)

FIG. 2B is a graph showing results of the antidepressant effects of R(−)- and S(+)-ketamine in the DEX-treated mice investigated by the LMT the day after the injection of ketamine. In FIG. 2B, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2B indicates locomotions (count/60 min). (Example 1)

FIG. 2C is a graph showing results of the antidepressant effects of R(−)- and S(+)-ketamine in the DEX-treated mice investigated by the TST the day (27 hours) after the injection of ketamine. In FIG. 2C, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2C indicates immobility times (sec) in the TST. (Example 1)

FIG. 2D is a graph showing results of the antidepressant effects of R(−)- and S(+)-ketamine in the DEX-treated mice investigated by the FST the day (29 hours) after the injection of ketamine. In FIG. 2D, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2D indicates immobility times (sec) in the FST. (Example 1)

FIG. 2E is a graph showing results of the antidepressant effects of R(−)- and S(+)-ketamine in the DEX-treated mice investigated by the SPT 2 days after the injection of ketamine. In FIG. 2E, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2E indicates sucrose preferences (%) in the SPT. (Example 1)

FIG. 2F is a graph showing results of the antidepressant effects of R(−)- and S(+)-ketamine in the DEX-treated mice investigated by the TST 7 days after the injection of ketamine. In FIG. 2F, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2F indicates immobility times (sec) in the TST. (Example 1)

FIG. 2G is a graph showing results of the antidepressant effects of R(−)- and S(+)-ketamine in the DEX-treated mice investigated by the FST 7 days after the injection of ketamine. In FIG. 2G, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2G indicates immobility times (sec) in the FST. (Example 1)

FIG. 3A is a diagram illustrating a test protocol for investigating antidepressant effects of R(−)- and S(+)-ketamine in social defeat stress mice. The social defeat stress mice were prepared by bringing C57/B6 male mice into contact with ICR male mice for 10 consecutive days (D1 to 10). After that, any one of R(−)-ketamine and S(+)-ketamine was injected and various tests were performed on day 1, day 2, day 6, and day 7 (P1, P2, P6, and P7) after the injection. In FIG. 3A, R-Ket and S-Ket represent social defeat stress mouse groups injected with R(−)-ketamine and S(+)-ketamine, respectively. Saline represents a social defeat stress mouse group injected with saline. In FIG. 3A, LMT means a locomotion test, TST means a tail suspension test, FST means a forced swimming test, and SPT means a 1% sucrose preference test. (Example 2)

FIG. 3B is a graph showing results of the antidepressant effects of R(−)- and S(+)-ketamine in the social defeat stress mice investigated by the SPT 1 day (P1) after the injection of ketamine. In FIG. 3B, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3B indicates sucrose preferences (%) in the SPT. (Example 2)

FIG. 3C is a graph showing results of the antidepressant effects of R(−)- and S(+)-ketamine in the social defeat stress mice investigated by the LMT 2 days (P2) after the injection of ketamine. In FIG. 3C, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3C indicates locomotions (count/60 min) in the LMT. (Example 2)

FIG. 3D is a graph showing results of the antidepressant effects of R(−)- and S(+)-ketamine in the social defeat stress mice investigated by the TST 2 days (P2) after the injection of ketamine. In FIG. 3D, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3D indicates immobility times (sec) in the TST. (Example 2)

FIG. 3E is a graph showing results of the antidepressant effects of R(−)- and S(+)-ketamine in the social defeat stress mice investigated by the FST 2 days (P2) after the injection of ketamine. In FIG. 3E, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3E indicates immobility times (sec) in the FST. (Example 2)

FIG. 3F is a graph showing results of the antidepressant effects of R(−)- and S(+)-ketamine in the social defeat stress mice investigated by the SPT 6 days (P6) after the injection of ketamine. In FIG. 3F, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3F indicates sucrose preferences (%) in the SPT. (Example 2)

FIG. 3G is a graph showing results of the antidepressant effects of R(−)- and S(+)-ketamine in the social defeat stress mice investigated by the TST 7 days (P7) after the injection of ketamine. In FIG. 3G, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3G indicates immobility times (sec) in the TST. (Example 2)

FIG. 3H is a graph showing results of the antidepressant effects of R(−)- and S(+)-ketamine in the social defeat stress mice investigated by the FST 7 days (P7) after the injection of ketamine. In FIG. 3H, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3H indicates immobility times (sec) in the FST. (Example 2)

FIG. 3I is a graph showing results of effects of R(−)- and S(+)-ketamine on the spine density of the frontal cortex in the social defeat stress mice investigated 8 days after the injection of ketamine. In FIG. 3I, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. In addition, mPFC means the medial prefrontal cortex. (Example 2)

FIG. 3J is a graph showing results of effects of R(−)- and S(+)-ketamine on the spine density of the hippocampal dentate gyrus in the social defeat stress mice investigated 8 days after the injection of ketamine. In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. (Example 2)

FIG. 3K is a graph showing results of effects of R(−)- and S(+)-ketamine on the spine density of the hippocampus CA1 region in the social defeat stress mice investigated 8 days after the injection of ketamine. In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. (Example 2)

FIG. 3L is a graph showing results of effects of R(−)- and S(+)-ketamine on the spine density of the hippocampus CA3 region in the social defeat stress mice investigated 8 days after the injection of ketamine. In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. (Example 2)

FIG. 3M is a graph showing results of effects of R(−)- and S(+)-ketamine on the spine density of the nucleus accumbens in the social defeat stress mice investigated 8 days after the injection of ketamine. In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. (Example 2)

FIG. 3N is a graph showing results of effects of R(−)- and S(+)-ketamine on the spine density of the striatum in the social defeat stress mice investigated 8 days after the injection of ketamine. In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. (Example 2)

FIG. 4 is a graph showing time-dependent changes in locomotion of control mice after the injection of R(−)- and S(+)-ketamine. In FIG. 4, R-Ket, S-Ket, and Saline represent groups injected with R(−)-ketamine, S(+)-ketamine, and saline, respectively. The ordinate axis of FIG. 4 indicates locomotion (count/10 min). (Example 3)

FIG. 5A is a graph showing changes in prepulse inhibition after the injection of R(−)-ketamine in control mice. In FIG. 5A, R-Ket and Saline represent groups injected with R(−)-ketamine and saline, respectively. PP69, PP73, PP77, and PP81 mean that stimuli at 69, 73, 77, and 81 dB for more than 20 milliseconds were presented 100 milliseconds before a 110-dB pulse, respectively. Data analysis was performed by Wilks Lambda, which is multivariate analysis of variance. (Example 3)

FIG. 5B is a graph showing changes in prepulse inhibition after the injection of S(+)-ketamine in the control mice. In FIG. 5B, S-Ket and Saline represent groups injected with S(+)-ketamine and saline, respectively. PP69, PP73, PP77, and PP81 mean that stimuli at 69, 73, 77, and 81 dB for more than 20 milliseconds were presented 100 milliseconds before a 110-dB pulse, respectively. Data analysis was performed by Wilks Lambda, which is multivariate analysis of variance. (Example 3)

FIG. 6A is a diagram illustrating a test protocol for investigating rewarding effects of R(−)-ketamine, S(+)-ketamine, and RS(+/−)-ketamine on the control mice using a conditioned place preference test. 15-minute habituation was performed for 3 days. Then, 30-minute conditioning was performed on day 4 to day 10, and a behavioral evaluation test was performed on day 11. Saline was injected on day 5, day 7, and day 9. In FIG. 6A, R-Ket, S-Ket, and RS-Ket mean groups injected with R(−)-ketamine, S(+)-ketamine, and RS(+/−)-ketamine, respectively. In each of the groups, the injection was performed three times, i.e., on day 4, day 6, and day 8. Saline means a group injected with saline. In the group, the injection was performed three times, i.e., on day 5, day 7, and day 9. (Example 3)

FIG. 6B is a graph showing results of the rewarding effects of R(−)-ketamine on the control mice using the conditioned place preference test. In FIG. 6B, R-Ketamine and Saline represent groups injected with R(−)-ketamine and saline, respectively. The ordinate axis of FIG. 6B indicates conditioned place preference test scores (CPP scores). (Example 3)

FIG. 6C is a graph showing results of the rewarding effects of S(+)-ketamine on the control mice using the conditioned place preference test. In FIG. 6C, S-Ketamine and Saline represent groups injected with S(+)-ketamine and saline, respectively. The ordinate axis of FIG. 6C indicates conditioned place preference test scores (CPP scores). (Example 3)

FIG. 6D is a graph showing results of the rewarding effects of RS(+/−)-ketamine on the control mice using the place preference test. In FIG. 6D, RS-Ketamine and Saline represent groups injected with RS(+/−)-ketamine and saline, respectively. The ordinate axis of FIG. 6D indicates conditioned place preference test scores (CPP scores). (Example 3)

DESCRIPTION OF EMBODIMENTS

The present invention relates to an agent for prevention and/or treatment of a depressive symptom, consisting of R(−)-ketamine or a pharmacologically acceptable salt thereof. The present invention also relates to a pharmaceutical composition for prevention and/or treatment of a depressive symptom, including R(−)-ketamine or a pharmacologically acceptable salt thereof in an effective amount for reducing a depressive symptom, and being substantially free of S(+)-ketamine or a pharmacologically acceptable salt thereof. The phrase "substantially free of S(+)-ketamine or a pharmacologically acceptable salt thereof" means that: S(+)-ketamine or a pharmacologically acceptable salt thereof is not contained at all; or S(+)-ketamine or a pharmacologically acceptable salt thereof may be contained in such an amount that its effects and side effects are not exhibited, or may be contained as such an impurity as to be mixed inevitably during the manufacture of the agent and the pharmaceutical composition.

Further, the present invention relates to a method of treating a depressive symptom, comprising administering R(−)-ketamine or a pharmacologically acceptable salt thereof to a subject, wherein the subject has been diagnosed with having a depressive symptom, in an amount effective to treat the depressive symptom. The present invention also relates to a method of treating a depressive symptom, comprising administering a pharmaceutical composition to a subject, wherein the pharmaceutical composition comprises R(−)-ketamine or a pharmaceutically acceptable salt thereof in an amount effective to treat a depressive symptom, and a pharmaceutically acceptable carrier, and being substantially free of S(+)-ketamine or a pharmacologically acceptable salt thereof, and wherein the subject has been diagnosed with having a depressive symptom.

Furthermore, the present invention also relates to use of R(−)-ketamine for the manufacture of a pharmaceutical composition for treating a depressive symptom.

In the present invention, through the use of a new animal model of depression, it was demonstrated that R(−)-ketamine had rapid and long-lasting antidepressant effects. The animal model was prepared by the inventors of the present application based on their finding that depression-like behavior was found in mice exposed neonatally to DEX at a juvenile stage and an adult stage (Non Patent Literature 18; see Example 1). The animal model exhibits depression-like behavior even at a juvenile stage, and hence is useful as an animal model of depression in children as well as depression in adults.

In the present invention, it was also revealed that R(−)-ketamine had antidepressant effects in a social defeat stress model as well. The social defeat stress model is a typical animal model of depression, which is used throughout the world (Non Patent Literature 19).

R(−)-ketamine exhibited rapid and long-lasting antidepressant effects on depression-like behaviors of the juvenile mice after the neonatal DEX exposure and the social defeat stress mouse model through its single administration (see Example 1 and Example 2). Meanwhile, in locomotion-enhancing effects, disruption of prepulse inhibition, and a dependence test using a conditioned place preference test, which are evaluation systems for side effects, significant changes were found in S(+)-ketamine, whereas such side effects were not found in R(−)-ketamine (see Examples 4, 5, and 6). In addition, in the conditioned place preference test, RS(+/−)-ketamine increased a conditioned place preference (CPP) score, indicating drug dependence of RS(+/−)-ketamine. Further, R(−)-ketamine has low affinity for the NMDA receptor as compared to S(+)-ketamine, and thus is considered to have less side effects such as psychotomimetic effects. Accordingly, R(−)-ketamine can serve as a promising and safe antidepressant as compared to S(+)-ketamine and RS(+/−)-ketamine.

R(−)-ketamine or a pharmacologically acceptable salt thereof may be used as an antidepressant, specifically, as an agent to be used for treatment and/or prevention of depressive symptoms such as mood depression, lowering of motivation, anxiety, the accompanying insomnia and anorexia, and suicidal ideation.

The agent and pharmaceutical composition according to the present invention are preferably applicable to diseases exhibiting depressive symptoms, for example, depression such as MDD or pediatric depression, and bipolar disorder involving a repeat of depressive symptoms and manic symptoms as their opposite symptoms, and are more preferably applicable to depression in children and depression in adults. In addition, it has been reported that ketamine is also effective for treatment-resistant obsessive-compulsive disorder and treatment-resistant PTSD (Non Patent Literatures 6, 7, and 8). Thus, the agent and pharmaceutical composition according to the present invention are preferably applicable to obsessive-compulsive disorder and PTSD. Obsessive-compulsive disorder, which is one type of anxiety disorder and is a disease with pathological conditions characterized by obsessions and compulsions, is considered to be associated with depression. Patients with obsessive-compulsive disorder have depression as well and exhibit depressive symptoms in addition to obsessions and compulsions in extremely many cases. Patients with PTSD exhibit depressive symptoms in many cases. In actuality, an antidepressant such as an SSRI is used as a therapeutic drug for PTSD, but its therapeutic effects are weak. The scope of the present invention encompasses a pharmaceutical composition for prevention and/or treatment of obsessive-compulsive disorder and PTSD, containing R(−)-ketamine or a pharmacologically acceptable salt thereof in an effective amount for reducing symptoms of obsessive-compulsive disorder and PTSD, and being substantially free of S(+)-ketamine or a pharmacologically acceptable salt thereof. In addition, ketamine treatment in an adult with autism spectrum has been reported (Non Patent Literature 10). Thus, the agent and pharmaceutical composition according to the present invention are preferably applicable to autism spectrum disorder. Furthermore, Depression in elderly peoples is known to increase the risk if incident dementia, in particular of Alzheimer's disease and vascular dementia (Non Patent Literature 1). Therefore, the agent and pharmaceutical composition according to the present invention is a potential preventive or therapeutic drug for dementia including Alzheimer's disease and vascular dementia.

The agent and pharmaceutical composition according to the present invention may be administered orally or parenterally. In the oral administration, a known dosage form for administration, including a tablet, a capsule, a coated tablet, a troche, or a liquid such as a solution or a suspension, may be used. In addition, examples of the parenteral administration may include: intravenous, intramuscular, or subcutaneous administration by injection; transmucosal administration such as transnasal or oral administration using a spray, an aerosol, or the like; rectal administration using a suppository or the like; and transdermal administration using a patch, a liniment, a gel, or the like. Preferred examples thereof may include oral administration, transnasal administration, and intravenous administration.

R(−)-ketamine may be used in both the forms of a free base and a pharmaceutically acceptable salt thereof. The pharmaceutically acceptable salt is preferably a pharmaceutically acceptable acid addition salt, more preferably a hydrochloride.

The chemical structural formula of R(−)-ketamine hydrochloride is represented by the following formula (I).

[Chem. 1]

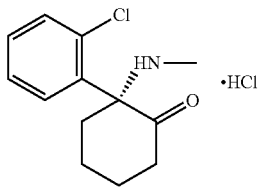

(I)

R(−)-ketamine or a pharmacologically acceptable salt thereof may be subjected to modification, for example, substitution of a chlorine molecule as a substituent by another halogen molecule and/or substitution of a methyl group as a substituent by another alkyl group, to thereby manufacture a derivative. As a result, a compound having more preferred effects may be obtained.

Further, when the compound according to the present invention is labeled with an isotope such as a stable isotope $^{13}C$ or $^{2}H$ (D), the compound can be measured for its in vivo kinetics and quantitatively measured for its affinity for the NMDA receptor in the brain, for example.

The pharmaceutical composition according to the present invention may contain, in addition to R(−)-ketamine or a pharmacologically acceptable salt thereof, other ingredients having drug efficacy that are effective for depressive symptoms, the ingredients being other than S(+)-ketamine. In addition, the pharmaceutical composition according to the present invention may appropriately contain, in addition to those ingredients having drug efficacy, an appropriate pharmaceutically acceptable carrier well known to those of ordinary skill in the art, depending on an administration form and the like. Examples of the pharmaceutically acceptable carrier may include an antioxidant, a stabilizer, a preservative, a taste-masking agent, a colorant, a solubilizer, a solubilizing agent, a surfactant, an emulsifier, an antifoaming agent, a viscosity adjustor, a gelling agent, an absorption accelerator, a dispersant, an excipient, and a pH adjustor.

When the agent and pharmaceutical composition according to the present invention are each prepared as a formulation for injection, it is preferred that the formulation be in the form of a solution or a suspension. When the agent and pharmaceutical composition are each prepared as a formulation for transmucosal administration such as transnasal or oral administration, it is preferred that the formulation be in the form of a powder, a drop, or an aerosol. In addition, when the agent and pharmaceutical composition are each prepared as a formulation for rectal administration, it is preferred that the formulation be in the form of a semi-solid formulation such as a cream or a suppository. Each of those formulations may be prepared by any one of the methods known to those skilled in the art of pharmacy as disclosed in, for example, Remington's Pharmaceutical Sciences (Mack Publishing Company, Easton, Pa., 1970). In the formulation for injection, for example, a plasma-derived protein such as albumin, an amino acid such as glycine, and a sugar such as mannitol may each be added as a carrier, and a buffer, a solubilizing aid, an isotonic agent, and the like may also be added. In addition, when the formulation is used as a water-soluble formulation or a lyophilized formulation, it is preferred to add a surfactant such as Tween™ 80 or Tween™ 20 in order to prevent aggregation. Further, a dosage form for parenteral administration other than the formulation for injection may contain distilled water or saline, polyalkylene glycol such as polyethylene glycol, a plant-derived oil, hydrogenated naphthalene, and the like. For example, a formulation for rectal administration such as a suppository contains general excipients such as polyalkylene glycol, petrolatum, and cacao oil and fat. A vaginal formulation may contain an absorption accelerator such as a bile salt, an ethylenediamine salt, and a citric acid salt. A formulation for inhalation may be solid, and may contain an excipient such as lactose. Further, a transnasal drop may be a water or oil solution.

The accurate dosage and dosing regimen of each of the agent and pharmaceutical composition according to the present invention may be adjusted depending on required amounts, treatment methods, diseases, degrees of necessity, or the like for individual treatment targets. The dosage may be specifically determined depending on an age, a body weight, a general health condition, a sex, a meal, an administration time, an administration method, an elimination rate, a combination of drugs, a medical condition of a patient, and the like, and may be determined in consideration of other factors. When the pharmaceutical composition according to the present invention is administered for diseases exhibiting depressive symptoms, such as depression, bipolar disorder, and obsessive-compulsive disorder, it is preferred that an active ingredient contained in the pharmaceutical composition be contained in an effective amount for reducing symptoms of the diseases such as depression, bipolar disorder, and obsessive-compulsive disorder, preferably depressive symptoms of the diseases. R(−)-ketamine or a pharmaceutically acceptable salt thereof can be safely used because of having less side effects found in S(+)-ketamine and RS(+/−)-ketamine. Its dosage per day varies depending on the condition and body weight of a patient, the kind of a compound, an administration route, and the like. For example, in terms of the amount of an active ingredient, it is desired that the dosage in the case of parenteral administration be from about 0.01 to 1,000 mg/person/day, preferably from 0.1 to 500 mg/person/day, and the dosage in the case of oral administration be from about 0.01 to 500 mg/person/day, preferably from 0.1 to 100 mg/person/day.

EXAMPLES

The present invention is hereinafter described in more detail by way of Examples. However, the present invention is by no means limited to Examples below. Further, various modifications are possible without departing from the technical concept of the present invention.

Example 1

A new animal model of depression (Non Patent Literature 18) was used to investigate antidepressant effects of R(−)- and S(+)-ketamine on the depression-like behavior of the animal model. All tests were performed under the approval of the Animal Care and Use Committee of Chiba University.

1. Materials and Methods

R(−)- and S(+)-ketamine hydrochloride were prepared from RS(+/−)-ketamine (Ketalar™, ketamine hydrochloride, Daiichi Sankyo Co., Ltd., Tokyo, Japan) using D(−)- and L(+)-tartaric acid, respectively, by the method disclosed in the previous report (Patent Literature 2) (FIG. 1). The purity of each of those isomers was confirmed by high-performance liquid chromatography (CHIRALPAK™ IA, column size: 250×4.6 mm, mobile phase; n-hexane/dichloromethane/diethylamine (75/25/0.1), retention time for S(+)-ketamine=6.99 min, retention time for R(−)-ketamine=10.56 min, Daicel Corporation, Tokyo, Japan).

A new animal model of depression was prepared by exposing mice neonatally to dexamethasone (hereinafter abbreviated as DEX). Through the neonatal DEX exposure, depression-like behavior was observed in each of juvenile mice and adult mice. Thus, the mouse model was shown to be able to serve as a novel animal model of depression. The mouse model was prepared and reported only recently by the inventors of the present application and their collaborators (Non Patent Literature 18). Specifically, the juvenile mice exposed neonatally to DEX and the adult mice exposed neonatally to DEX showed a significant decrease in novel object search time in a novel object recognition test as compared to control mice, which indicated a reduction in social learning property in the model mice. In addition, in a social memory test, the mice exposed neonatally to DEX showed a significant decrease in stimulation target follow-up time, which indicated a reduction in social recognition ability. In an open field test, a time spent in the center of a field significantly decreased, which indicated a reduction in spontaneous activity. In a light-dark box test, a time spent in a white box significantly decreased, which indicated that anxiety-like behavior was caused. In each of a tail suspension test (TST) and a forced swimming test (FST), an increase in immobility time was found, which indicated that depression-like behavior was shown. Meanwhile, in a locomotion test (LMT), there was no difference in locomotion between the mice exposed to DEX and the control mice. Further, alterations were found in levels of amino acids (glutamate, glutamine, glycine, D-serine, and L-serine) in mouse brains after the neonatal DEX exposure (Non Patent Literature 18). Those amino acids are known to be associated with NMDA receptor mediated neurotransmission. Thus, it is conceivable that alterations in glutamatergic transmission via the NMDA receptor after the neonatal DEX exposure may be involved in the depression-like behavior in the juvenile mice and the adult mice (Non Patent Literature 18).

The preparation of the animal model of depression and the administration of the agent were specifically performed as described below (FIG. 2A). Male and female ICR mice (9-week-old, Japan SLC, Inc., Hamamatsu, Japan) were used. The mice were given free access to water and feed. A breeding procedure consisted of housing three to four females with one male, for 14 days. On the final day of this period, the females were placed in isolation and checked daily around the expected delivery day. The day of birth was defined as day 0. The mice were injected intraperitoneally with DEX (Wako Pure Chemical Industries, Ltd., Tokyo, Japan) dissolved in saline on day 1, day 2, and day 3 at doses of 0.5 mg/kg body weight, 0.3 mg/kg body weight, and 0.1 mg/kg body weight, respectively. In addition, normal controls were injected with equal volumes (10 ml/kg) of saline. R(−)- or S(+)-ketamine at a dose of 10 mg/kg body weight or vehicle (saline 10 ml/kg) was injected intraperitoneally into male juvenile mice on day 36 after the birth.

The antidepressant effects of the agent were investigated for juvenile mice by behavioral tests such as the TST, the FST, the LMT, and a 1% sucrose preference test (SPT) (FIG. 2A). The TST and the FST were performed twice, i.e., the day (27 hours and 29 hours, respectively) and 7 days after the injection of ketamine, and the LMT and the SPT were performed on the day and 2 days after the injection of ketamine. The TST was performed as described below. First, the mice were taken out from cages, and then a small piece of an adhesive tape was bonded onto a portion approximately 2 cm away from the tip of the tail of the mice. A small hole was opened in the small piece, and the mice were each fixed upside down on a hook through the small hole. The immobility time of each mouse was recorded for 10 minutes. Mice were considered immobile only when they hung passively and completely motionless. The immobility time increases in a depressive state. The FST was performed as described below. First, the mice were placed individually in a cylinder (diameter: 23 cm; height: 31 cm) containing 15 cm of water, maintained at 22 to 24 deg C. The mice were tested in an automated forced-swimming apparatus using SCANET MV-40 (MELQUEST Co., Ltd., Toyama, Japan). The immobility time was calculated as a value obtained by subtracting active time from total time, using the analysis software of the apparatus. Cumulative immobility time was recorded over 6 minutes during a test period. The LMT was performed as described below. First, the mice were placed in experimental cages (length×width×height: 560×560×330 mm). The locomotor activity of the mice was counted with SCANET MV-40, and the cumulative exercise of the mice was recorded for 60 minutes. The cages were cleaned between testing session. The immobility time increases in a depressive state. The SPT was performed by preparing general drinking water and a 1% sucrose solution so that the mice had free access thereto, and measuring the ratio of the amount of the sucrose solution consumed. The consumption of the sucrose solution, which is a reward response, reduces in a depressive state.

Statistical analysis was performed by one-way analysis of variance (one-way ANOVA), followed by a least significant difference test (LSD test). Data are presented as the mean plus minus standard error of the mean (n=8 to 12 mice/group). $p<0.05$,  $p<0.01$, and * $p<0.001$ indicate significant differences as compared to a DEX-treated mouse group injected with saline, and $^{\#}p<0.05$ and $^{\#\#}p<0.01$ indicate significant differences as compared to a DEX-treated mouse group injected with S(+)-ketamine.

2. Results

Significant increases in immobility time in the TST and the FST and a reduction in sucrose consumption preference in the SPT were found in the mice exposed neonatally to DEX as compared to the control mice. On the other hand, in the LMT, there was no difference in locomotion between the DEX-treated mice and the control mice.

In the LMT performed on the day after the injection of both the isomers of ketamine, there was no difference in locomotion among the control mice, the DEX-treated mice injected with saline, and the DEX-treated mice injected with R(−)- or S(+)-ketamine (FIG. 2B).

In the TST and FST performed on the day after the injection of both the isomers of ketamine, significant increases in immobility time were found in the DEX-treated mice injected with saline as compared to the control mice. Each of both the isomers of ketamine markedly reduced the immobility time increased in the DEX-treated mice 27 hours or 29 hours after its injection (FIGS. 2C and 2D). R(−)-ketamine exhibited slightly high antidepressant effects as compared to those of S(+)-ketamine, although no significant difference was found there between.

In the SPT performed on 2 days after the injection of both the isomers of ketamine, a reduction in sucrose consumption preference was found in the DEX-treated mice injected with saline as compared to the control mice. Both the isomers of ketamine significantly restored the sucrose consumption preference reduced in the DEX-treated mice 48 hours after their injection (FIG. 2E).

In the TST and FST performed on 7 days after the injection of both the isomers of ketamine, significant increases in immobility time were found in the DEX-treated mice injected with saline as compared to the control mice. In addition, R(−)-ketamine significantly reduced the immobility time increased in the DEX-treated mice, whereas S(+)-ketamine did not reduce the immobility time increased in the DEX-treated mice. The differences between R(−)-ketamine and S(+)-ketamine were found to be statistically significant (FIGS. 2F and 2G).

The above-mentioned results revealed that R(−)- and S(+)-ketamine at a dose of 10 mg/kg exhibited antidepressant effects in the juvenile mice after the neonatal DEX exposure (days 1 to 3). In the TST and the FST, the antidepressant effects of both the isomers of ketamine were found 27 to 29 hours after their single injection. It is noteworthy that in the TST and the FST, the antidepressant effects of R(−)-ketamine were able to be detected even 7 days after its single injection, whereas the antidepressant effects of S(+)-ketamine were not able to be detected 7 days after its single injection. The results show that R(−)-ketamine has more long-lasting antidepressant effects than S(+)-isomer. Both the isomers of ketamine are known to exhibit a rapid in vivo clearance. Despite the fact that R(−)-ketamine is considered to be eliminated from the body by 7 days after its single injection, the antidepressant effects were found. This indicates that the differences in antidepressant effects 7 days after the injection of both the isomers of ketamine do not result from differences in pharmacokinetics.

Example 2

A social defeat stress model of depression (Non Patent Literature 19) was used to investigate antidepressant effects of R(−)- and S(+)-ketamine on the depression-like behavior of the animal model. All tests were performed under the approval of the Animal Care and Use Committee of Chiba University.

1. Materials and Methods

R(−)- and S(+)-ketamine hydrochloride were prepared from RS(+/−)-ketamine (Ketalar™, ketamine hydrochloride, Daiichi Sankyo Co., Ltd., Tokyo, Japan) using D(−)- and L(+)-tartaric acid, respectively, by the method disclosed in the previous report (Patent Literature 2) (FIG. 1). The purity of each of those isomers was confirmed by high-performance liquid chromatography (CHIRALPAK™ IA, column size: 250×4.6 mm, mobile phase; n-hexane/dichloromethane/diethylamine (75/25/0.1), retention time for S(+)-ketamine=6.99 min, retention time for R(−)-ketamine=10.56 min, Daicel Corporation, Tokyo, Japan).

A social defeat stress model of depression was prepared by bringing C57/B6 male mice into contact with ICR male mice (large aggressive mice) for 10 consecutive days to apply a stress called a "social defeat stress" in accordance with the previous report (Non Patent Literature 19). Depression-like behavior was observed in the mice that had received the social defeat stress. Specifically, an increase in immobility time was found in each of a tail suspension test (TST) and a forced swimming test (FST). In addition, in a 1% sucrose preference test, the ratio of sucrose water drunk significantly reduced, suggesting that depression-like behavior (e.g. anhedonia) was shown. On the other hand, in a locomotion test (LMT), there was no difference in locomotion between social defeat stress mice and control mice.

The preparation of the animal model of depression and the administration of the agent were specifically performed as described below (FIG. 3A). Male C57/B6 mice (7-week-old, Japan SLC, Inc., Hamamatsu, Japan) and ICR mice (9-week-old, Japan SLC, Inc., Hamamatsu, Japan) were used. The mice were given free access to water and feed. A social defeat stress was applied by housing one C57/B6 mouse with one ICR mouse for 10 days. On day 11, a social interaction test was performed to select mice exhibiting depressive symptoms, which were used for the subsequent behavioral evaluation. Control mice were injected with vehicle (saline 10 ml/kg) and the mice exhibiting depressive symptoms were injected intraperitoneally with R(−)- or S(+)-ketamine at a dose of 10 mg/kg body weight, or vehicle (saline 10 ml/kg).

The antidepressant effects of the agent were investigated by behavioral tests such as the TST, the FST, the LMT, and a 1% sucrose preference test (SPT) (FIG. 3A). The 1% sucrose preference test (SPT) was performed on 1 day and 6 days after the injection of ketamine. Each of the TST and the FST was performed on 2 days and 7 days after the injection of ketamine. The TST was performed as described below. First, the mice were taken out from cages, and then a small piece of an adhesive tape was bonded onto a portion approximately 2 cm away from the tip of the tail of the mice. A small hole was opened in the small piece, and the mice were each fixed upside down on a hook through the small hole. The immobility time of each mouse was recorded for 10 minutes. Mice were considered immobile only when they hung passively and completely motionless. The immobility time increases in a depressive state. The FST was performed as described below. First, the mice were placed individually in a cylinder (diameter: 23 cm; height: 31 cm) containing 15 cm of water, maintained at 22 to 24 deg C. The mice were tested in an automated forced-swimming apparatus using SCANET MV-40 (MELQUEST Co., Ltd., Toyama, Japan). The immobility time was calculated as a value obtained by subtracting active time from total time, using the analysis software of the apparatus. Cumulative immobility time was recorded over 6 minutes during a test period. The LMT was performed as described below. First, the mice were placed in experimental cages (length×width×height: 560×560×330 mm). The locomotor activity of the mice was counted with SCANET MV-40, and the cumulative exercise of the mice was recorded for 60 minutes. The cages were cleaned between testing session. The immobility time increases in a depressive state. The SPT was performed by preparing general drinking water and a 1% sucrose solution so that the mice had free access thereto, and measuring the ratio of the amount of the sucrose solution consumed. The consumption of the sucrose solution, which is a reward response, reduces in a depressive state. The mice were decapitated 5 days after the injection of ketamine, and the brain was quickly dissected out and subjected to Golgi staining. A spine density was quantitatively evaluated by observation with a KEYENCE microscope (BZ-9000, Osaka, Japan).

The statistical analysis of the results of the social defeat stress model was performed by one-way analysis of variance (one-way ANOVA), followed by a least significant difference test (LSD test). Data are presented as the mean plus minus standard error of the mean (n=8 to 11 mice/group). *$p<0.05$, $p<0.01$, and *$p<0.001$ indicate significant differences as compared to a social defeat stress mouse group injected with saline, and #$p<0.05$ indicates a significant difference as compared to a social defeat stress mouse group injected with S(+)-ketamine.

2. Results

Significant increases in immobility time in the TST and the FST and a significant reduction in sucrose consumption preference in the SPT were found in the social defeat stress mice as compared to the control mice. On the other hand, in the LMT, there was no difference in locomotion between the social defeat stress mice and the control mice.

In the SPT performed on 1 day after the injection of both the isomers of ketamine, in the social defeat stress mice, the sucrose consumption preference significantly decreased as compared to the control group, and depressive symptoms were exhibited. In the social defeat stress mouse group injected with R(−)- or S(+)-ketamine, the sucrose consumption preference significantly increased as compared to the social defeat stress mouse group injected with saline, and depressive symptoms were alleviated. In addition, the antidepressant effects of R(−)-ketamine were more potent than those of S(+)-ketamine (FIG. 3B).

In the LMT performed on 2 days after the injection of both the isomers of ketamine, there was no difference in locomotion among the normal mice, the social defeat stress mice injected with saline, and the social defeat stress mice injected with R(−)- or S(+)-ketamine (FIG. 3C).

In the TST and FST performed on 2 days after the injection of both the isomers of ketamine, significant increases in immobility time were found in the social defeat stress mice injected with saline as compared to the control mice. Each of both the isomers of ketamine markedly reduced the immobility time increased in the social defeat stress mice 2 days after its injection (FIGS. 3D and 3E). R(−)-ketamine exhibited significant high antidepressant effects as compared to those of S(+)-ketamine (FIGS. 3D and 3E).

In the SPT performed on 6 days after the injection of both the isomers of ketamine, a reduction in sucrose consumption preference was found in the social defeat stress mice injected with saline as compared to the control mice. Both the isomers of ketamine significantly restored the sucrose consumption preference reduced in the social defeat stress mice 6 days after their injection. The difference between R(−)-ketamine and S(+)-ketamine was found to be statistically significant (FIG. 3F).

In the TST and FST performed on 7 days after the injection of both the isomers of ketamine, significant increases in immobility time were found in the social defeat stress mice injected with saline as compared to the control mice. Each of both the isomers of ketamine significantly reduced the immobility time increased in the social defeat stress mice 7 days after its injection (FIGS. 3G and 3H). R(−)-ketamine exhibited significantly high antidepressant effects as compared to S(+)-ketamine (FIGS. 3G and 3H).

In the Golgi staining performed 8 days after the injection of both the isomers of ketamine, a significant decrease in spine density was found in the frontal cortex and hippocampal dentate gyrus of the social defeat stress mice injected with saline as compared to the control mice. Each of both the isomers of ketamine significantly improved the decreased density of spine in the social defeat stress mice 8 days after its injection (FIGS. 3I and 3J). In the hippocampal dentate gyrus, R(−)-ketamine showed more significant improvement in the restoration of spine density as compared to S(+)-ketamine (FIG. 3J). In the hippocampus CA1 region and striatum, no apparent change in spine density was observed (FIGS. 3K and 3N), while in hippocampus CA3 region, a decrease in spine density by social defeat stress was observed, which was significantly improved by R(−)-ketamine and S(+)-ketamine (FIG. 3L). In the nucleus accumbens, a significant increase in spine density was observed by social defeat stress, which was significantly improved by R(−)-ketamine and S(+)-ketamine (FIG. 3M).

The above-mentioned results revealed that R(−)- and S(+)-ketamine at a dose of 10 mg/kg exhibited antidepressant effects in the social defeat stress mice. It is noteworthy that in the SPT, the TST, and the FST, the antidepressant effects of R(−)-ketamine were significantly potent as compared to the effects of S(+)-ketamine. The results show that R(−)-ketamine has more long-lasting antidepressant effects than S(+)-isomer. Both the isomers of ketamine are known to exhibit a rapid in vivo clearance. Despite the fact that R(−)-ketamine is considered to be eliminated from the body by 7 days after its single injection, the antidepressant effects were found. This indicates that the differences in antidepressant effects 7 days after the injection of both the isomers of ketamine do not result from differences in pharmacokinetics.

Example 3

Control C57/B6 mice was used to investigate side effects of R(−)- and S(+)-ketamine. All tests were performed under the approval of the Animal Care and Use Committee of Chiba University.

1. Materials and Methods

The preparation of R(−)- and S(+)-ketamine hydrochloride and the confirmation of their purities were performed by the methods described in Example 2.

The administration of an agent was performed by the same methods as the methods described in Example 2.

The side effects of R(−)- and S(+)-ketamine were investigated by a locomotion-enhancing effect, disruption of prepulse inhibition, and a dependence test using a conditioned place preference test, which were systems for evaluating side effects.

An effect of ketamine on the locomotion of mice was tested using SCANET MV-40 (MELQUEST Co., Ltd., Toyama, Japan). Specifically, the locomotion was measured for a total of 180 minutes, i.e., 60 minutes before injection to 120 minutes after injection, and calculated as a locomotion per 10 minutes. The statistical analysis of the results of the locomotion was performed by repeated one-way analysis of variance (repeated one-way ANOVA), followed by a least significant difference test (LSD test). Data are presented as the mean plus minus standard error of the mean (n=7 or 8 mice/group). $p<0.01$ and *$p<0.001$ indicate significant differences as compared to a group injected with saline.

The prepulse inhibition test was performed using a startle response system (SR-LAB, San Diego Instruments, San Diego, Calif., United States). The analysis of the results of prepulse inhibition was performed by multivariate analysis of variance (MANOVA), followed by a least significant difference test (LSD test). Data are presented as the mean plus minus standard error of the mean (n=10 to 12 mice/group). *$p<0.05$ and ** $p<0.01$ indicate significant differences as compared to a group injected with saline.

The place preference test was performed using a conditioned place preference test apparatus (BrainSienceIdea Co., Ltd., Osaka, Japan). The analysis of the results of the place preference test was performed by one-way analysis of variance (one-way ANOVA), followed by a least significant difference test (LSD test). Data are presented as the mean plus minus standard error of the mean (n=9 or 10 mice/group). *$p<0.05$ and **$p<0.01$ indicate significant differences as compared to a group injected with saline.

2. Results

In the measurement of the locomotion after the injection of both the isomers of ketamine, a significant increase in locomotion was found 10 minutes and 20 minutes after the injection in the mice injected with S(+)-ketamine (10 mg/kg or 20 mg/kg) as compared to the control mice injected with saline. The locomotion was transiently enhanced by S(+)-ketamine (10 mg/kg or 20 mg/kg), but returned to a normal value 30 minutes after the injection. On the other hand, the injection of R(−)-ketamine (5, 10, or 20 mg/kg) did not affect the locomotion (FIG. 4).

In the prepulse inhibition test after the injection of both the isomers of ketamine, the injection of S(+)-ketamine (5, 10 mg/kg, or 20 mg/kg) disrupted prepulse inhibition in a dose-dependent manner (FIG. 5B). On the other hand, the injection of R(−)-ketamine (5, 10, or 20 mg/kg) did not disrupt prepulse inhibition (FIG. 5A).

In the conditioned place preference test after the injection of both the isomers and racemic mixture of ketamine, the injection of S(+)-ketamine (5, 10 mg/kg, or 20 mg/kg) increased the CPP score in a dose-dependent manner, indicating drug abuse potential (FIG. 6C). On the other hand, the injection of R(−)-ketamine (5, 10, or 20 mg/kg) did not increase the CPP score (FIG. 6B), indicating no drug abuse potential. In addition, the injection of RS(+/−)-ketamine (10 mg/kg) significantly increased the CPP score, indicating drug abuse potential (FIG. 6D).

As described above, from the viewpoint of side effects, the injection of S(+)-ketamine was found to exhibit a locomotion-enhancing effect, disrupt prepulse inhibition, and produce drug dependence. In addition, it was suggested that the injection of RS(+/−)-ketamine also produced drug dependence. On the other hand, R(−)-ketamine does not exhibit a locomotion-enhancing effect, disrupt prepulse inhibition, and produce drug dependence, for example, and hence is an agent having high safety as compared to RS(+/−)-ketamine and S(+)-ketamine that are clinically used at present.

INDUSTRIAL APPLICABILITY

As described above, the agent and pharmaceutical composition for prevention and/or treatment of a depressive symptom according to the present invention have rapid and long-lasting antidepressant effects and less side effects such as psychotomimetic effects, and hence are useful as novel pharmaceuticals in the field of prevention and/or treatment of a number of psychiatric diseases exhibiting depressive symptoms.

The invention claimed is:

1. A method of treating major depressive disorder, dementia, suicidal ideation, mood depression, low motivation, anxiety, insomnia, or anorexia in an adult subject in need thereof comprising administering a therapeutically effective amount of R(−)-ketamine or a pharmaceutically acceptable salt thereof, wherein the R(−)-ketamine or a pharmaceutically acceptable salt thereof is substantially free of S(+)-ketamine or a pharmaceutically acceptable salt thereof.

2. The method of claim 1, wherein the adult is an elderly adult.

3. The method of claim 1, wherein the subject in need thereof has been diagnosed with depression or a depressive symptom.

4. The method of claim 1, wherein the dementia is Alzheimer's disease, vascular dementia, or a combination thereof.

5. The method of claim 1, wherein the pharmaceutical composition being substantially free of S(+)-ketamine or a pharmaceutically acceptable salt thereof comprises no S(+)-ketamine or a pharmaceutically acceptable salt thereof.

6. The method of claim 1, wherein the pharmaceutical composition being substantially free of S(+)-ketamine or a pharmaceutically acceptable salt thereof comprises such an amount that side effects of S(+)-ketamine or a pharmaceutically acceptable salt thereof are not exhibited.

7. The method of claim 6, wherein the side effects comprise psychotomimetic effects.

8. The method of claim 1, wherein the therapeutically effective amount is about 0.01 mg/day to about 500 mg/day.

9. The method of claim 1, wherein the therapeutically effective amount is about 0.1 mg/day to about 500 mg/day.

10. The method of claim 1, wherein the therapeutically effective amount is about 0.1 mg/day to about 100 mg/day.

11. The method of claim 1, wherein the R(−)-ketamine or a pharmaceutically acceptable salt thereof is therapeutically effective 24 hours after administration to the subject.

12. The method of claim 1, wherein the R(−)-ketamine or a pharmaceutically acceptable salt thereof is therapeutically effective 48 hours after administration to the subject.

13. The method of claim 1, wherein the R(−)-ketamine or a pharmaceutically acceptable salt thereof is therapeutically effective at least 6 days after administration to the subject.

14. The method of claim 1, wherein the R(−)-ketamine or a pharmaceutically acceptable salt thereof is therapeutically effective at least 7 days after administration to the subject.

15. The method of claim 1, wherein the R(−)-ketamine or a pharmaceutically acceptable salt thereof is administered as a pharmaceutical composition further comprising a pharmaceutically acceptable carrier.

* * * * *